US012751701B2

(12) United States Patent
O'Neill et al.

(10) Patent No.: US 12,751,701 B2
(45) Date of Patent: Oct. 6, 2026

(54) APPARATI, INSTRUMENTS, SYSTEMS AND METHODS OF USE AND ASSEMBLY

(71) Applicant: STRYKER CORPORATION, Portage, MI (US)

(72) Inventors: Michael O'Neill, Charleston, SC (US); Garrett Deborst, Rockland, MA (US)

(73) Assignee: STRYKER CORPORATION, Portage, MI (US)

( * ) Notice: Subject to any disclaimer, the term of this patent is extended or adjusted under 35 U.S.C. 154(b) by 201 days.

(21) Appl. No.: 18/526,941

(22) Filed: Dec. 1, 2023

(65) Prior Publication Data

US 2025/0176951 A1 Jun. 5, 2025

(51) Int. Cl.
*A61B 10/02* (2006.01)

(52) U.S. Cl.
CPC ........ *A61B 10/0275* (2013.01); *A61B 10/025* (2013.01); *A61B 10/0283* (2013.01); *A61B 2010/0258* (2013.01)

(58) Field of Classification Search
CPC ............ A61B 10/0233; A61B 10/0241; A61B 10/025; A61B 10/0266; A61B 10/0275; A61B 2010/0208; A61B 2010/0258; A61B 17/1635; A61B 17/3205; A61B 17/32053; A61B 17/322; A61B 2017/320064; A61B 2017/3225
USPC ................................ 600/562, 564, 567, 568
See application file for complete search history.

(56) References Cited

U.S. PATENT DOCUMENTS 4,782,833 A 11/1988 Einhorn
4,951,690 A 8/1990 Baker
5,395,379 A * 3/1995 Deutchman ........ A61B 10/0283 604/227
5,577,517 A 11/1996 Bonutti
5,766,134 A 6/1998 Lisak
5,833,628 A 11/1998 Yuan
5,873,886 A 2/1999 Larsen
5,954,671 A 9/1999 O'Neill
6,022,354 A 2/2000 Mercuri
6,139,509 A 10/2000 Yuan
RE40,796 E 6/2009 O'Neill
8,162,850 B2 4/2012 Parihar
8,740,811 B2 * 6/2014 Fortems ............ A61B 10/0233 600/566
9,078,638 B2 7/2015 Wuestemann
9,192,396 B2 11/2015 Marino
10,039,601 B2 8/2018 Kim
(Continued)

FOREIGN PATENT DOCUMENTS

WO 2012011079 1/2012

OTHER PUBLICATIONS

International Search Report & Written Opinion of International Application No. PCT/US2024/057785, Mar. 25, 2025, 14 pages.

*Primary Examiner* — Adam J Eiseman
(74) *Attorney, Agent, or Firm* — DUANE MORRIS LLP

(57) ABSTRACT

An apparatus including a cylinder with a first end and a second end, a passive check valve with a first end and a second end, wherein the passive check valve is positioned at at least one of the first end and the second end of the cylinder, and a harvesting member coupled to the first end of the cylinder. A harvesting system includes an apparatus and a removal attachment coupled to the apparatus. Surgical methods for harvesting tissue from a patient using the apparatus are also disclosed.

8 Claims, 24 Drawing Sheets

(56) References Cited

U.S. PATENT DOCUMENTS

| | | | | |
|---|---|---|---|---|
| 10,123,786 | B2 | 11/2018 | Rocha-Singh | |
| 10,292,688 | B2 | 5/2019 | Marino | |
| 10,456,155 | B2 | 10/2019 | Salehi | |
| 11,020,244 | B2 | 6/2021 | Bays | |
| 11,090,092 | B2 | 8/2021 | O'Halloran | |
| 11,185,339 | B2 | 11/2021 | Perez | |
| 2007/0166834 | A1 | 7/2007 | Williamson, IV et al. | |
| 2009/0187116 | A1 | 7/2009 | Noishiki et al. | |
| 2010/0016878 | A1 | 1/2010 | Smith | |
| 2013/0053725 | A1* | 2/2013 | Beck | A61B 10/025<br>600/567 |
| 2013/0317507 | A1 | 11/2013 | Khanna et al. | |
| 2015/0045799 | A1 | 2/2015 | Budyansky et al. | |
| 2017/0340455 | A1 | 11/2017 | Greter et al. | |
| 2018/0000465 | A1 | 1/2018 | Brown | |
| 2018/0125465 | A1* | 5/2018 | Muse | A61B 17/3472 |
| 2018/0147071 | A1 | 5/2018 | Budyansky et al. | |
| 2019/0029657 | A1 | 1/2019 | Gulev | |
| 2019/0321015 | A1 | 10/2019 | Bagwan | |
| 2021/0186526 | A1 | 6/2021 | Budyansky et al. | |
| 2022/0087660 | A1* | 3/2022 | Schaubhut | A61B 10/0233 |
| 2022/0218945 | A1 | 7/2022 | Herrin | |
| 2022/0296801 | A1 | 9/2022 | Conlan et al. | |
| 2023/0338045 | A1* | 10/2023 | Kidman | A61B 17/1642 |

* cited by examiner

APPARATI, INSTRUMENTS, SYSTEMS AND METHODS OF USE AND ASSEMBLY

TECHNICAL FIELD

The present disclosure relates generally to apparati, instruments and systems for collecting bone, bone marrow, tissue, cells, fat or fluids. More specifically, but not exclusively, the present disclosure relates to apparatus, instruments, systems and methods for harvesting and/or collecting bone, bone marrow, tissue, cells, fat or fluids for bone graft harvesting, cancer biopsies, bone marrow aspirations, and the like.

BACKGROUND OF THE INVENTION

Many currently available apparatus, instruments, systems, and surgical methods for procedures involving harvesting or collecting bone, bone marrow, tissue, fat, and fluids from a patient do not address potential risk factors for pain and morbidity for patients. Currently, bone graft is utilized in orthopedic, neurosurgical, maxillofacial, and podiatry surgical procedures to promote bone fusion of one bone to another. A wide range of bone graft materials can be used to achieve bone fusion, including bone graft substitutes and composites, drug activated biologics, allograft from other humans, and autograft from the patient's own bones. Autograft is currently the preferred bone graft material because of its concentration of cells, signaling factors, and natural scaffold. Autograft is obtained from a variety of anatomical locations, generally the hip, tibia, femur, ulna, and calcaneus. Surgeons usually harvest the autograft using hand-held instruments, such as, chisels, gouges, and curettes, which require larger incisions to obtain sufficient bone grafts.

Additionally, surgeons may use some newer minimally-invasive instrumentation, such as, orthopedic hand tools, metal trephines, bone grinders, and coring drills to obtain bone grafts from patients. These instruments are often used in small bone fusion procedures, such as, foot and ankle, hand, and oral-maxillofacial procedures to obtain the needed autograft. The metal trephine and coring devices are generally attached to a power-driven coring device. During these procedures, a small incision is made above the bone to be harvested, such as, the calcaneus, tibia, ulna, or femur, and the metallic harvester is inserted into the donor site. Multiple passes are typically needed to harvest sufficient autograft based on the effectiveness of the harvester and overall graft requirements. When multiple passes are needed to obtain adequate bone, a large defect is created in the bone increasing risk of fracture and morbidity.

Although the currently available minimally-invasive instrumentation has in some cases improved surgical times, incision size, pain, and morbidity, there still remain deficiencies in these devices. For example, coring devices used in small bone surgeries are generally metallic, therefore, physicians are blinded to the contents obtained and must remove the instruments from the power driver to inspect the quality and quantity of bone collected within the coring devices. If there is not enough bone collected to meet the surgical requirements, the device is re-attached onto the drill and re-inserted into the donor site to obtain more bone material. By not being able to visualize within the coring devices, it is impossible to determine the amount and quality of material collected in the donor site, and also the fluid state acting within the coring device. In certain bones, such as the calcaneus, the donor sites are more fluid than in other donor sites, such as the iliac crest. In more fluid environments, when coring devices are used the graft that they collect is subject to a "vacuum" phenomenon, which can cause the collected bone to unknowingly be pulled out of the collection chambers of the coring devices. For example, as the coring devices are withdrawn proximally from the harvest site, a void is created and in order to equalize the pressure in the void, air is pulled through the coring device. As air is pulled through the coring device the collected graft material is pulled back out, thus, harvesting in a fluid environment can require more passes to obtain the necessary bone quantity needed for the patient's surgery. In some metallic devices a removable collection tray or window has been added, however, even with additional options, these devices can experience the collected graft material to be pulled out of the devices during removal from the harvest site.

In other currently available devices, drill bits, needles, chisels, gauges, and curettage are used to harvest bone graft some include suction systems that allow for bone and fluids to be drawn into a collection reservoir. In some devices, a motorized actuation is connected to an active vacuum to pull the bone into the cannula. In other devices, a vacuum source is used to pull liquids or solids through a lumen with the use of a hand-powered piston that produces a vacuum effect or pulling force to collect the graft.

Thus, it is an object of the present disclosure to overcome one or more of the above-described drawbacks and/or disadvantages of the currently available systems.

SUMMARY OF THE INVENTION

The present disclosure is directed toward apparatus, instruments, systems, and methods for collecting bone, tissue, and fluids.

In one aspect of the present disclosure provided herein, is an apparatus. The apparatus includes a cylinder with a first end and a second end, a passive check valve with a first end and a second end, wherein the passive check valve is positioned at at least one of the first end and the second end of the cylinder, and a harvesting member coupled to the first end of the cylinder.

In another aspect of the present disclosure provided herein is a harvesting system. The system includes an apparatus and a removal attachment coupled to the apparatus. The apparatus including a cylinder with a first end and a second end, a passive check valve with a first end and a second end, wherein the passive check valve is positioned at at least one of the first end and the second end of the cylinder, and a harvesting member coupled to the first end of the cylinder.

In yet another aspect of the present disclosure provided herein is a surgical method for harvesting bone, bone graft, bone marrow, tissue, fat, and/or fluid of a patient.

These and other objects, features and advantages of this disclosure will become apparent from the following detailed description of the various aspects of the disclosure taken in conjunction with the accompanying drawings.

BRIEF DESCRIPTION OF THE DRAWINGS

The accompanying drawings, which are incorporated in and constitute a part of the specification, illustrate embodiments of the disclosure and together with the detailed description herein, serve to explain the principles of the disclosure. It is emphasized that, in accordance with the standard practice in the industry, various features are not drawn to scale. In fact, the dimensions of the various features may be arbitrarily increased or reduced for clarity of discussion. The drawings are only for purposes of illustrating preferred embodiments and are not to be construed as limiting the disclosure.

DETAILED DESCRIPTION FOR CARRYING OUT THE INVENTION

Figure 1:
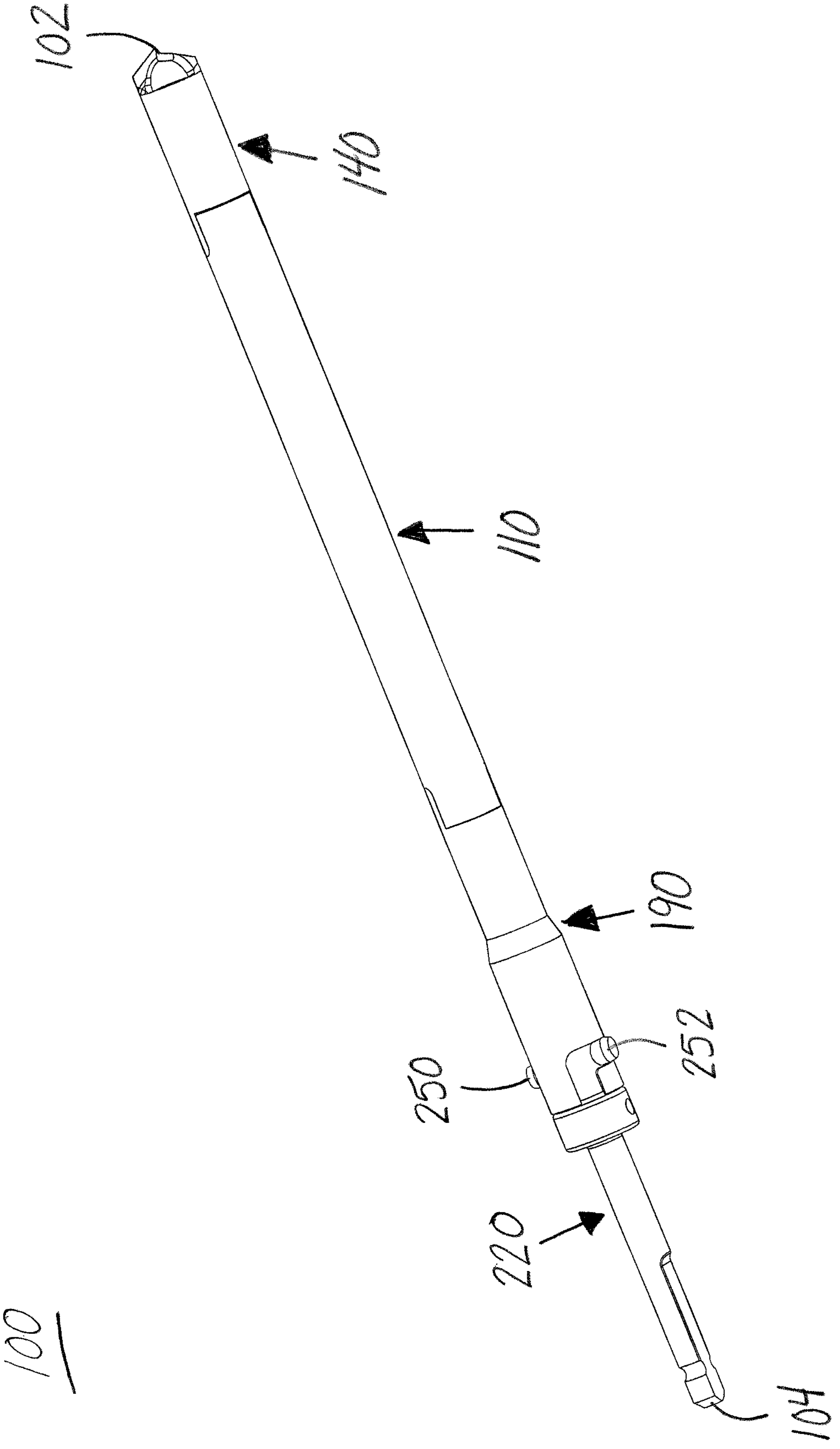
FIG. 1 is a first perspective view of an apparatus, in accordance with an aspect of the present disclosure.
Figure 2:
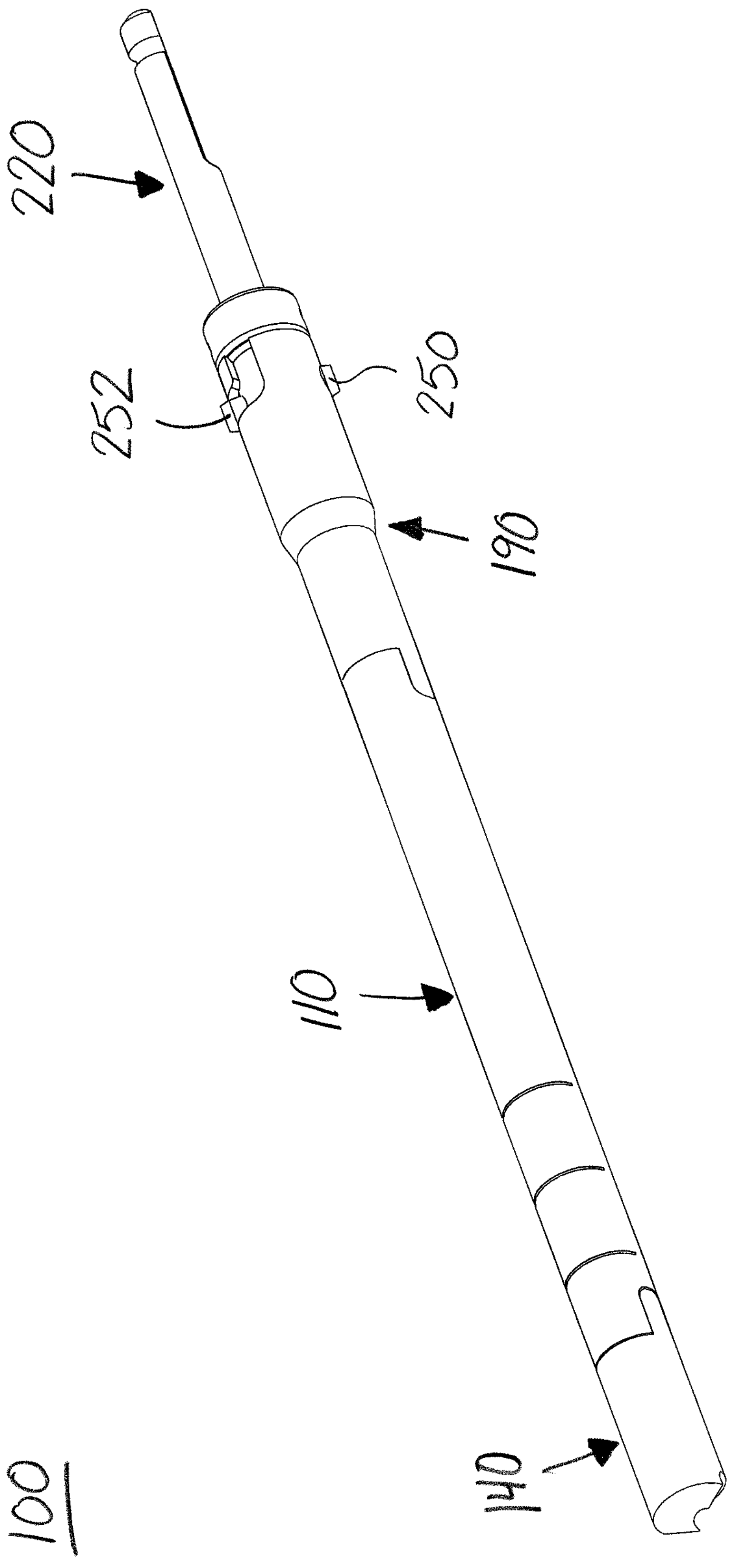
FIG. 2 is a second perspective view of the apparatus of FIG. 1, in accordance with an aspect of the present disclosure.
Figure 3:
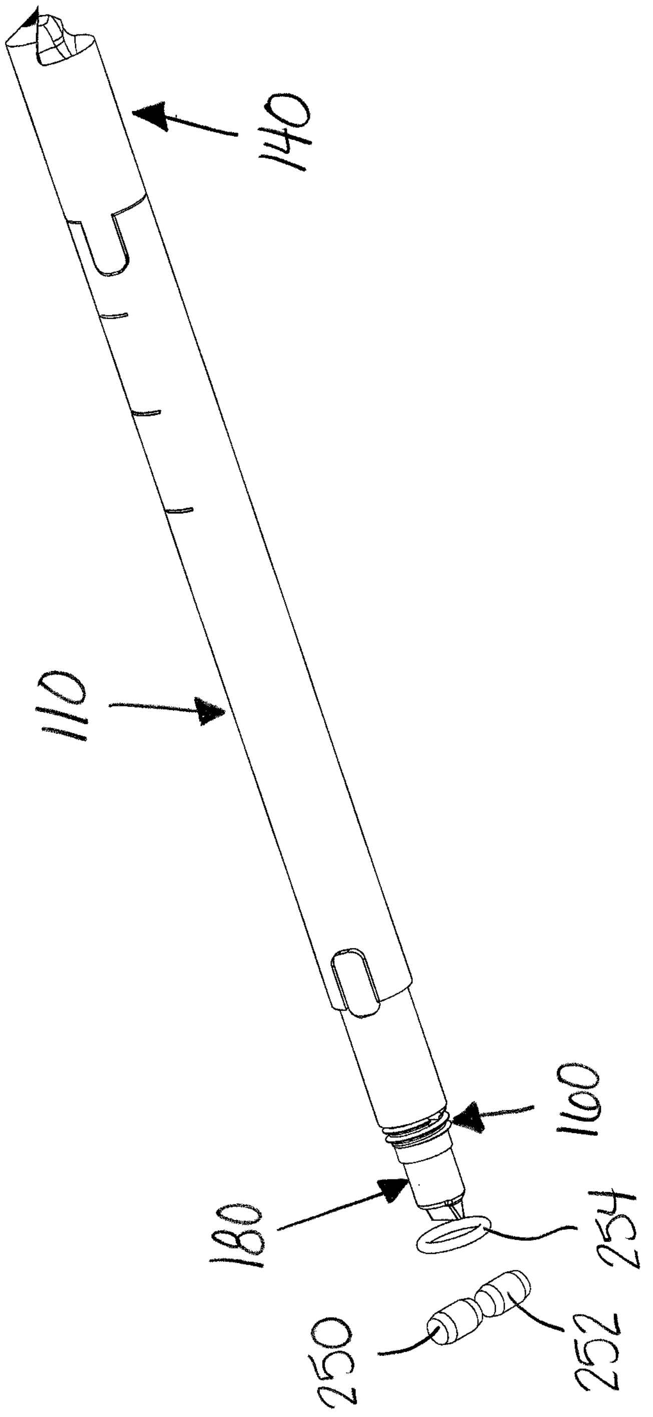
FIG. 3 is the first perspective view of the apparatus of FIG. 1 with the drive member and the shaft removed, in accordance with an aspect of the present disclosure.
Figure 4:
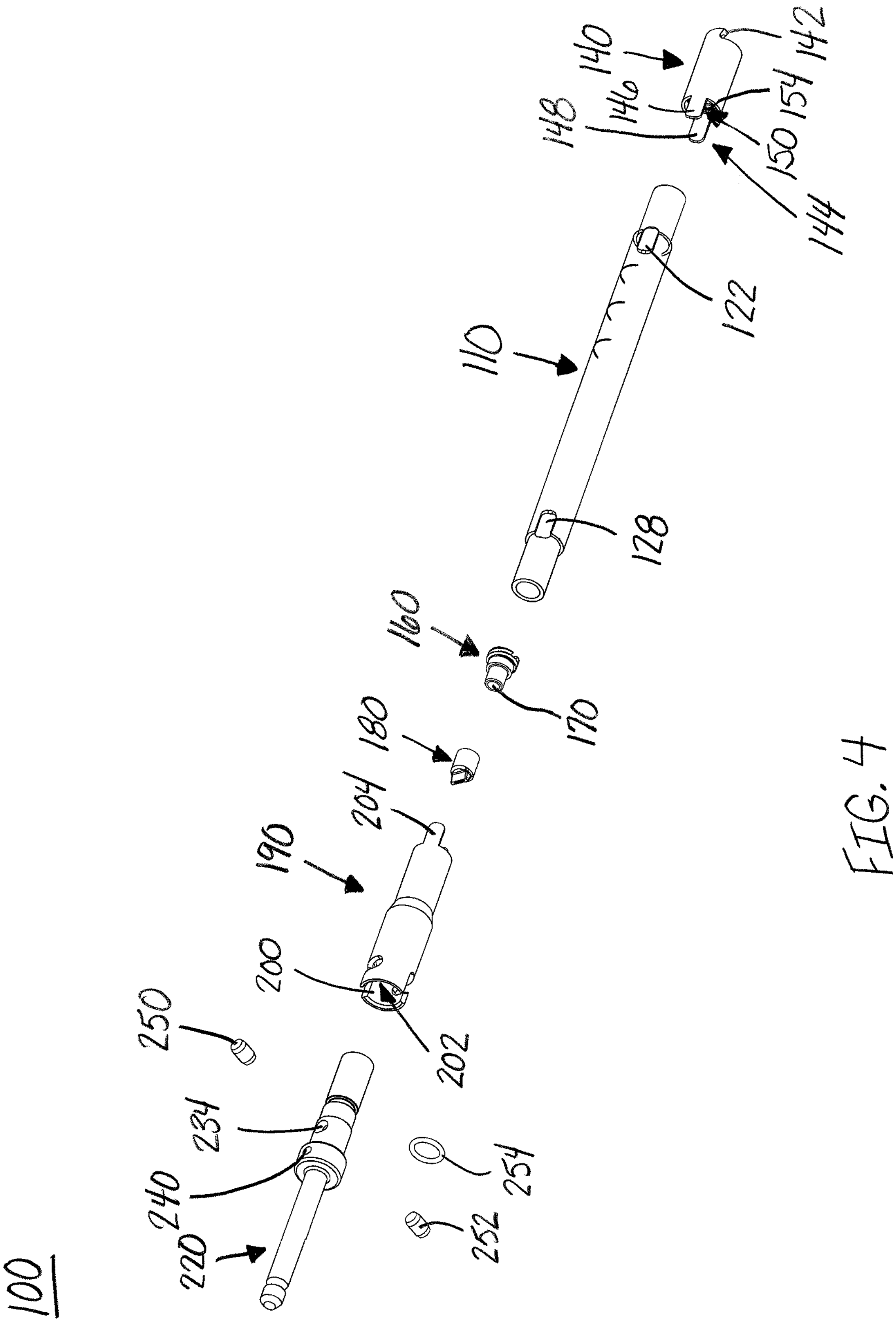
FIG. 4 is an exploded, first perspective view of the apparatus of FIG. 1, in accordance with an aspect of the present disclosure.
Figure 5:
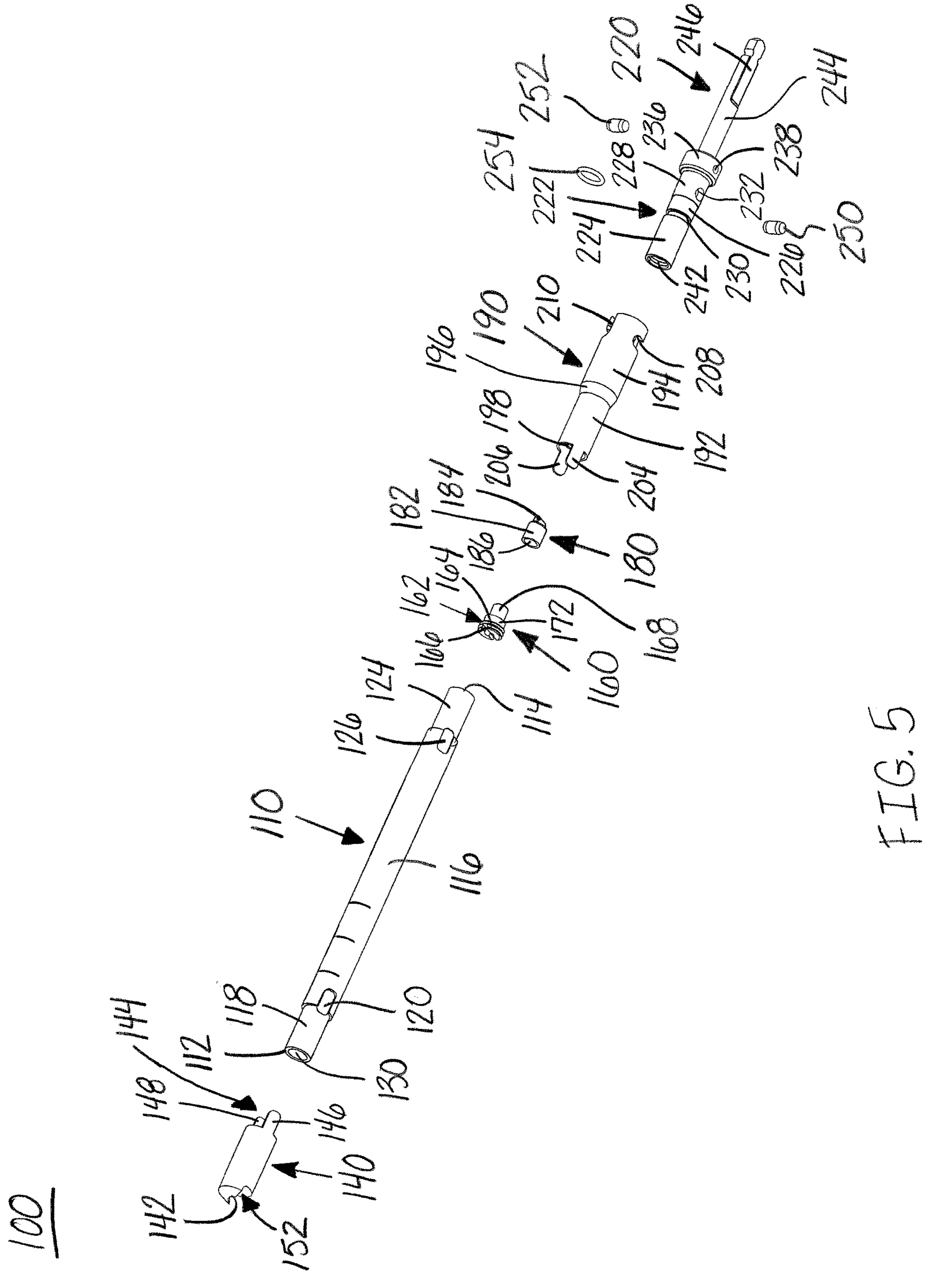
FIG. 5 is an exploded, second perspective view of the apparatus of FIG. 1, in accordance with an aspect of the present disclosure.
Figure 6:
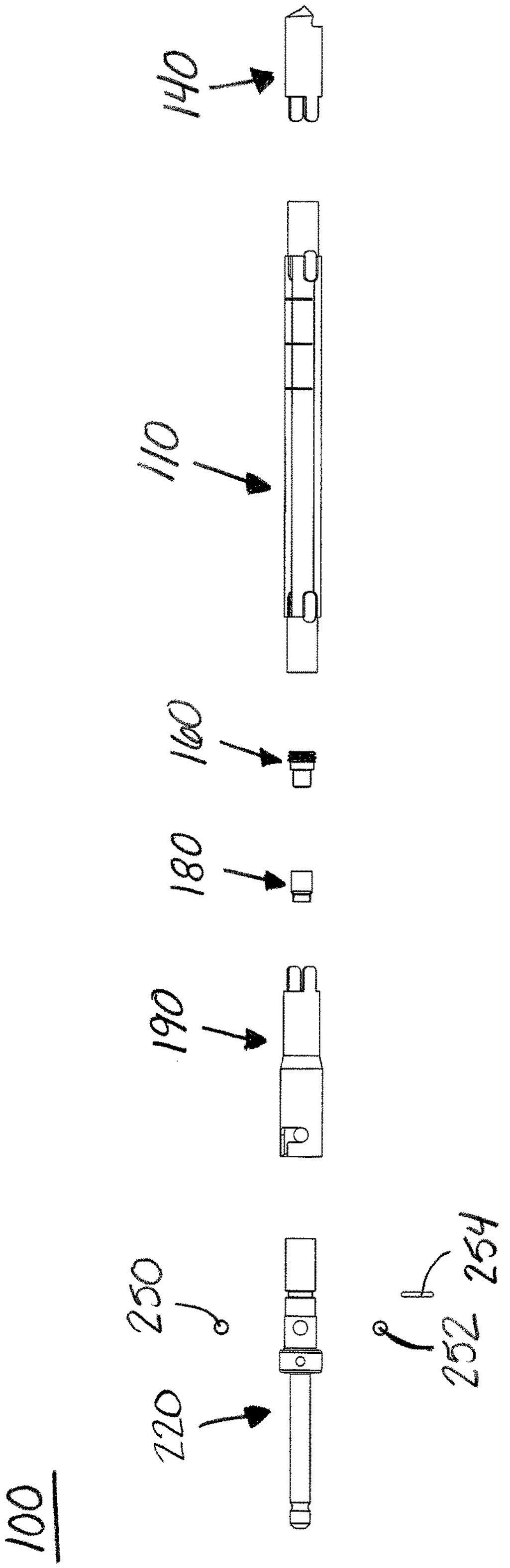
FIG. 6 is an exploded, first side view of the apparatus of FIG. 1, in accordance with an aspect of the present disclosure.
Figure 7:
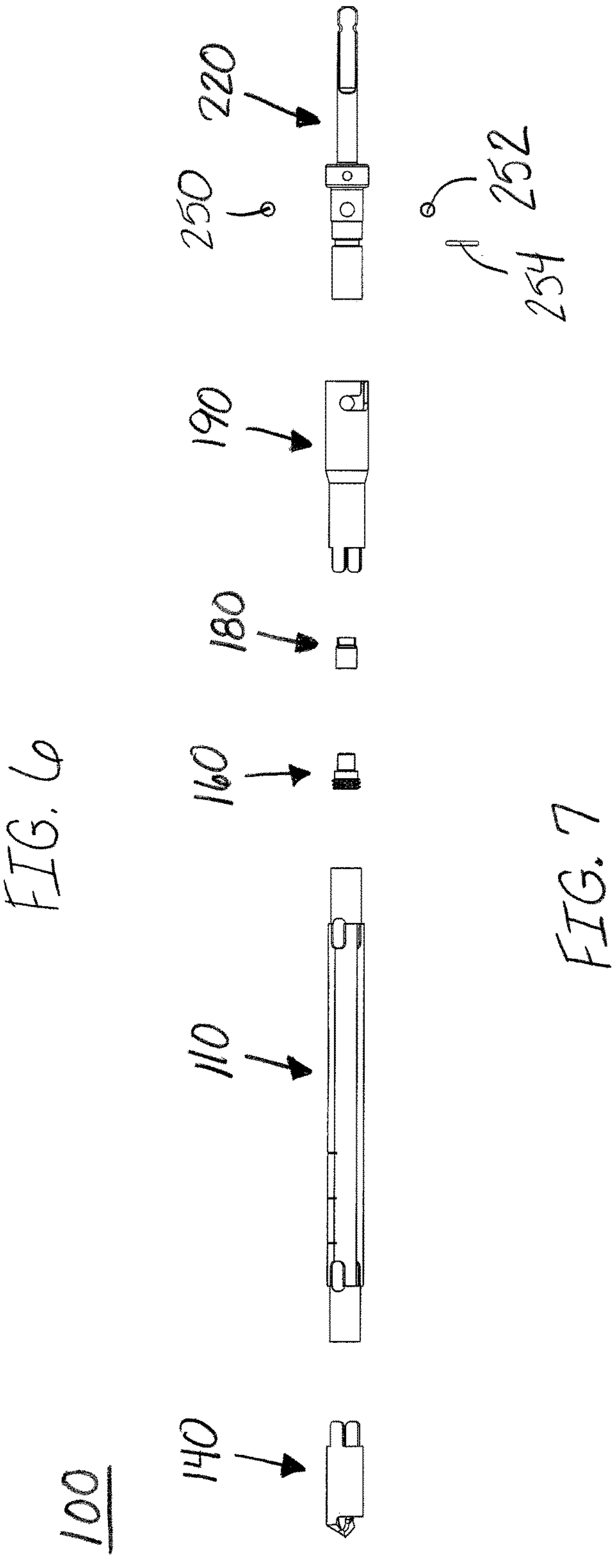
FIG. 7 is an exploded, second side view of the apparatus of FIG. 1, in accordance with an aspect of the present disclosure.
Figure 8:
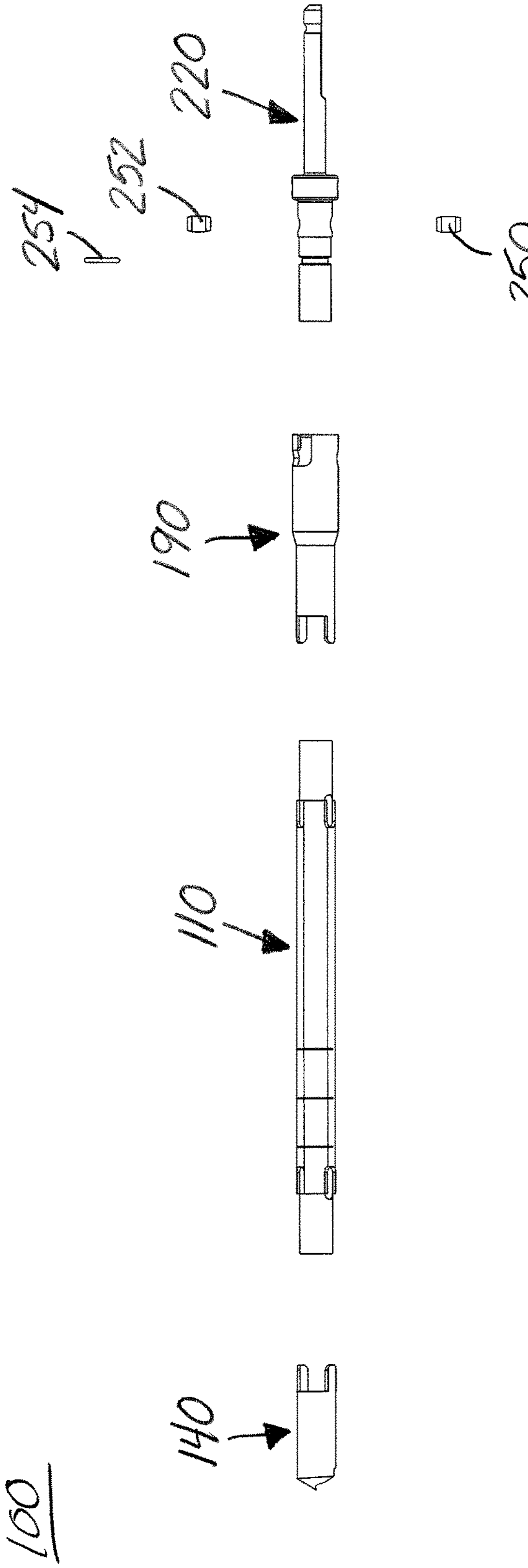
FIG. 8 is an exploded, top view of the apparatus of FIG. 1, in accordance with an aspect of the present disclosure.
Figure 9:
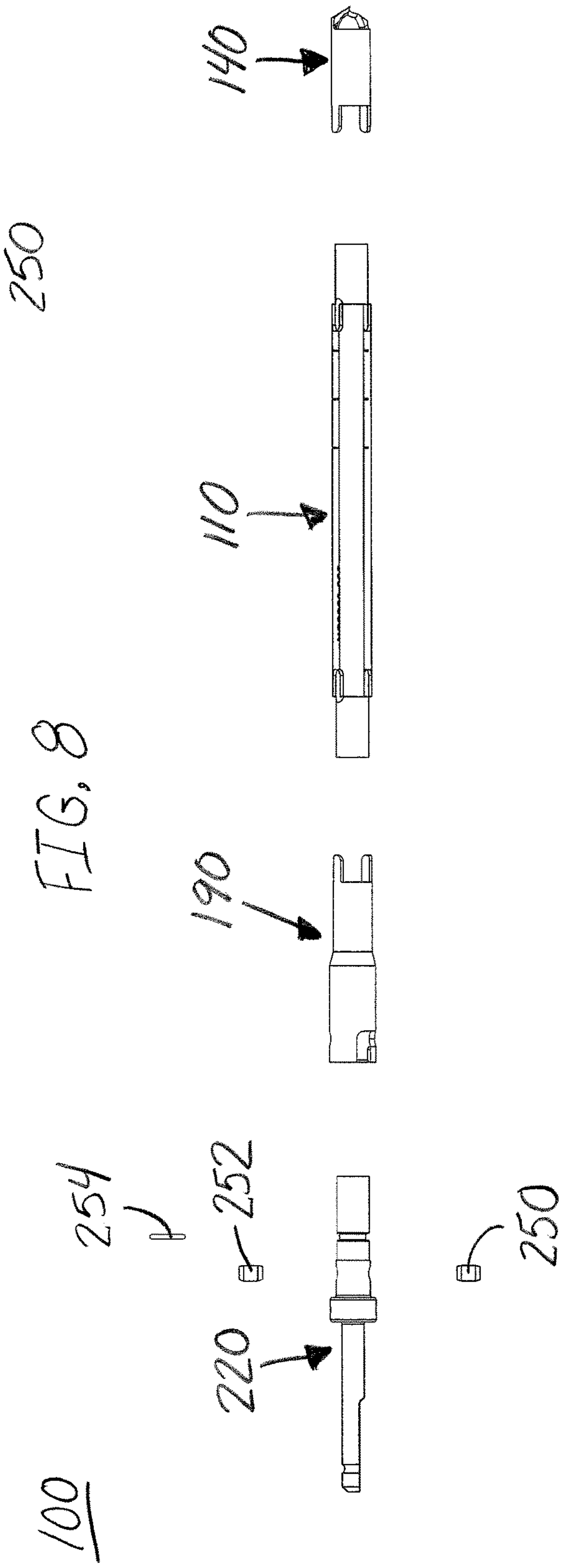
FIG. 9 is an exploded, bottom view of the apparatus of FIG. 1, in accordance with an aspect of the present disclosure.
Figure 10:
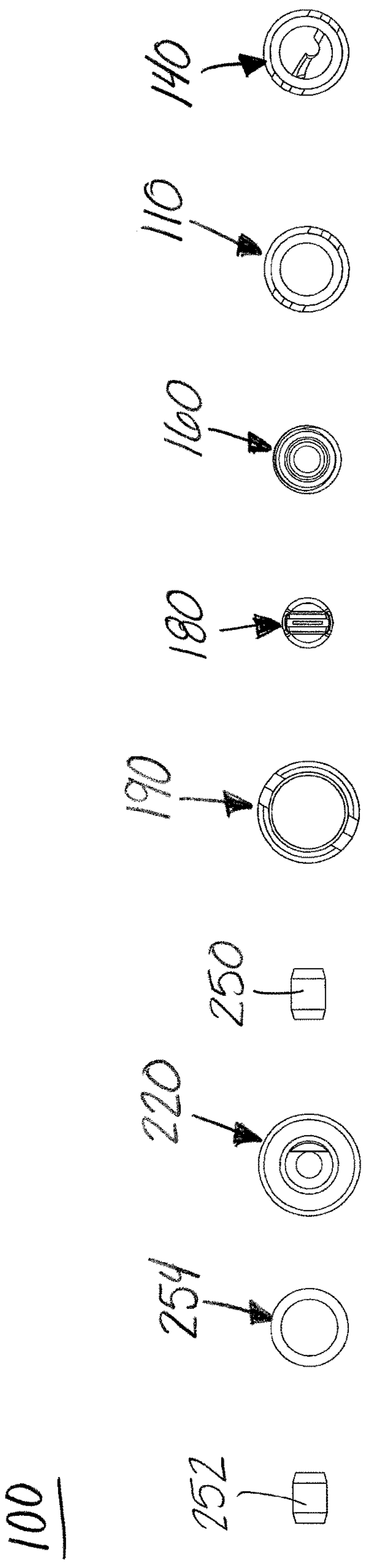
FIG. 10 is a first end view of the apparatus of FIG. 1, in accordance with an aspect of the present disclosure.
Figure 11:
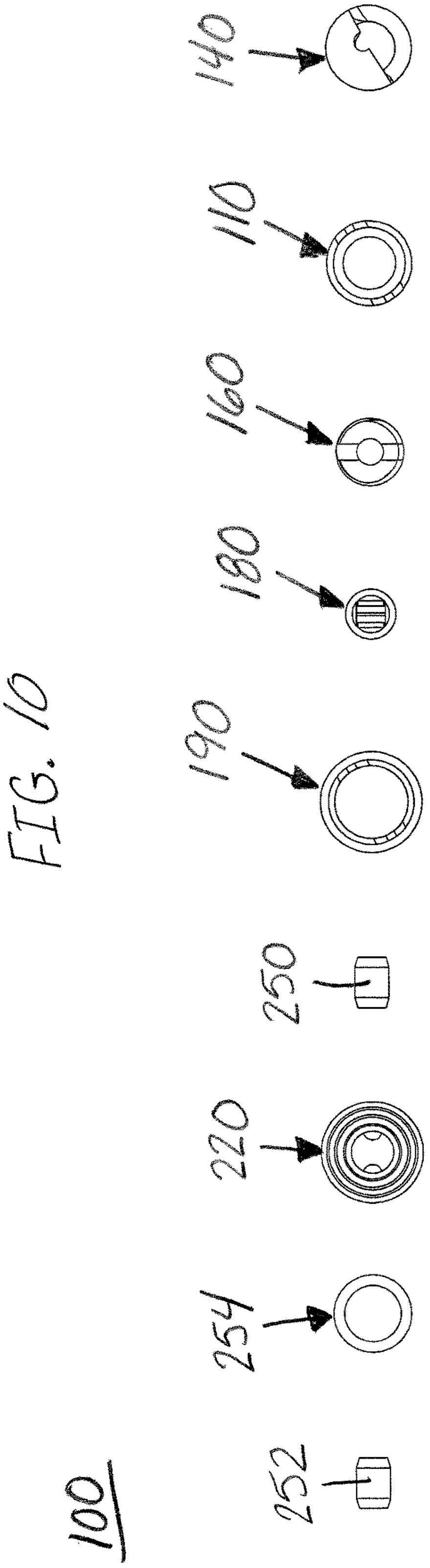
FIG. 11 is a second end view of the apparatus of FIG. 1, in accordance with an aspect of the present disclosure.
Figure 12:
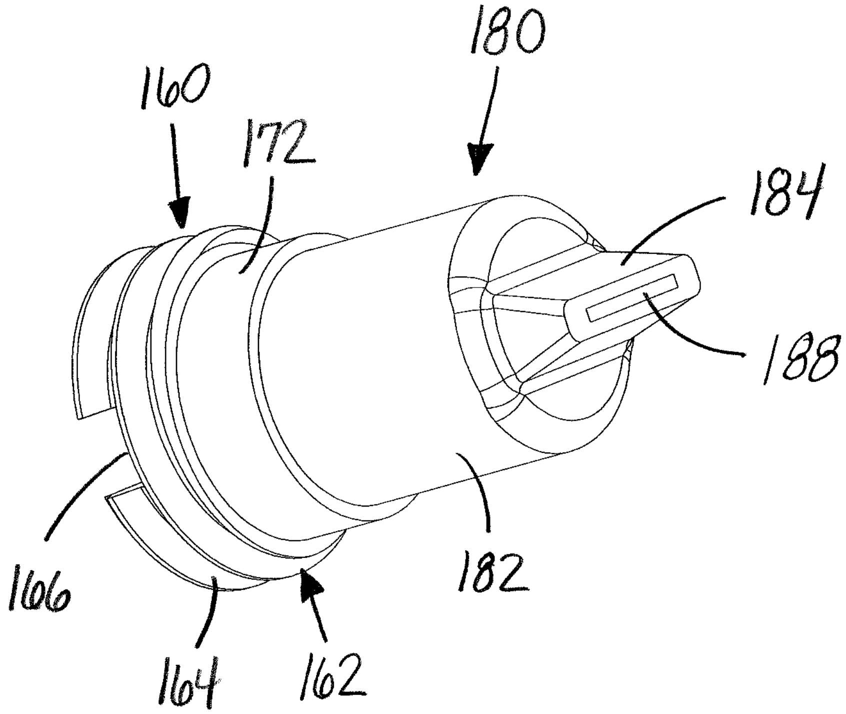
FIG. 12 is a first perspective view of a valve system of the apparatus of FIG. 1, in accordance with an aspect of the present disclosure.
Figure 13:
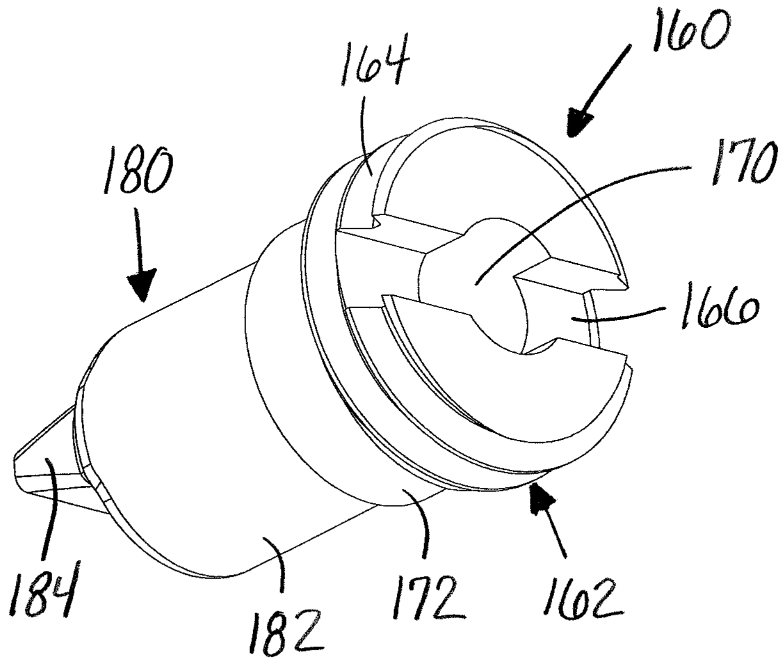
FIG. 13 is a second perspective view of the valve system of FIG. 12, in accordance with an aspect of the present disclosure.
Figure 14:
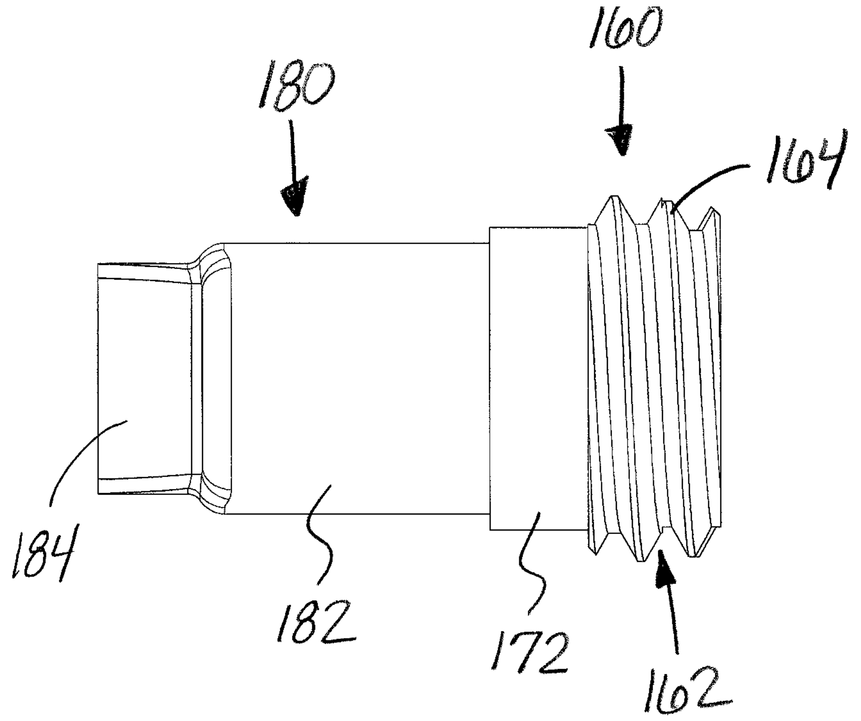
FIG. 14 is a top view of the valve system of FIG. 12, in accordance with an aspect of the present disclosure.
Figure 15:
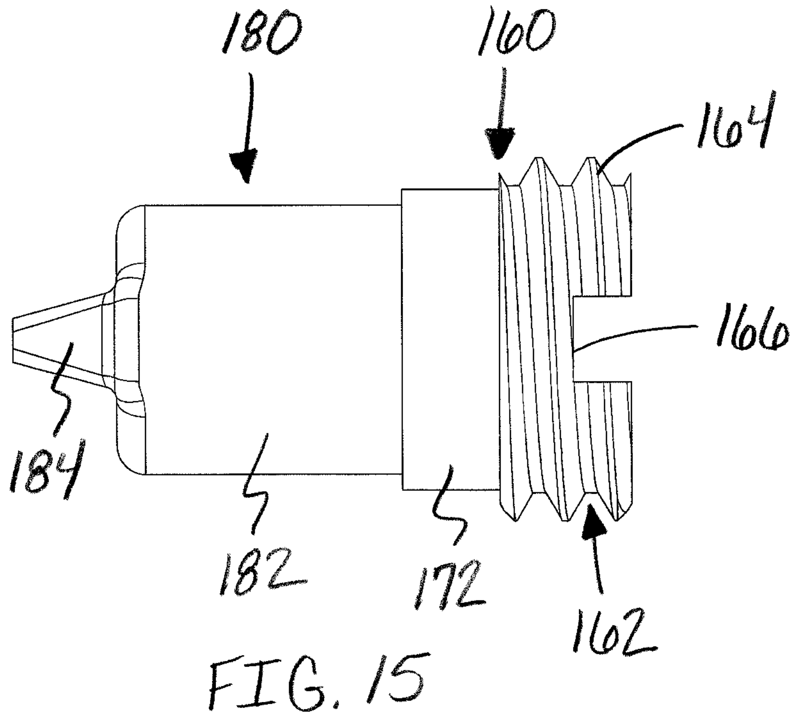
FIG. 15 is a side view of the valve system of FIG. 12, in accordance with an aspect of the present disclosure.
Figure 16:
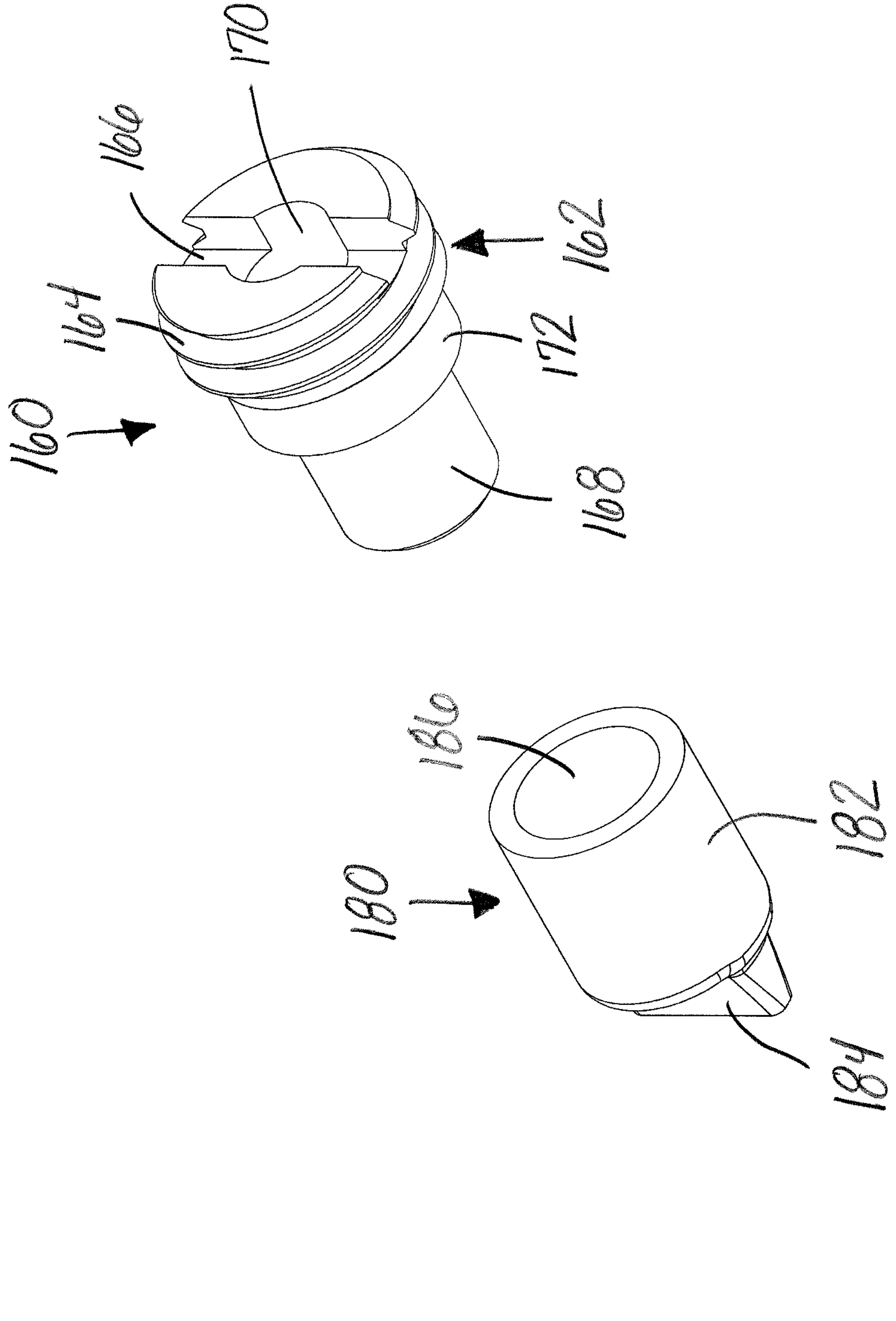
FIG. 16 is an exploded, first perspective view of the check valve system of FIG. 12, in accordance with an aspect of the present disclosure.
Figure 17:
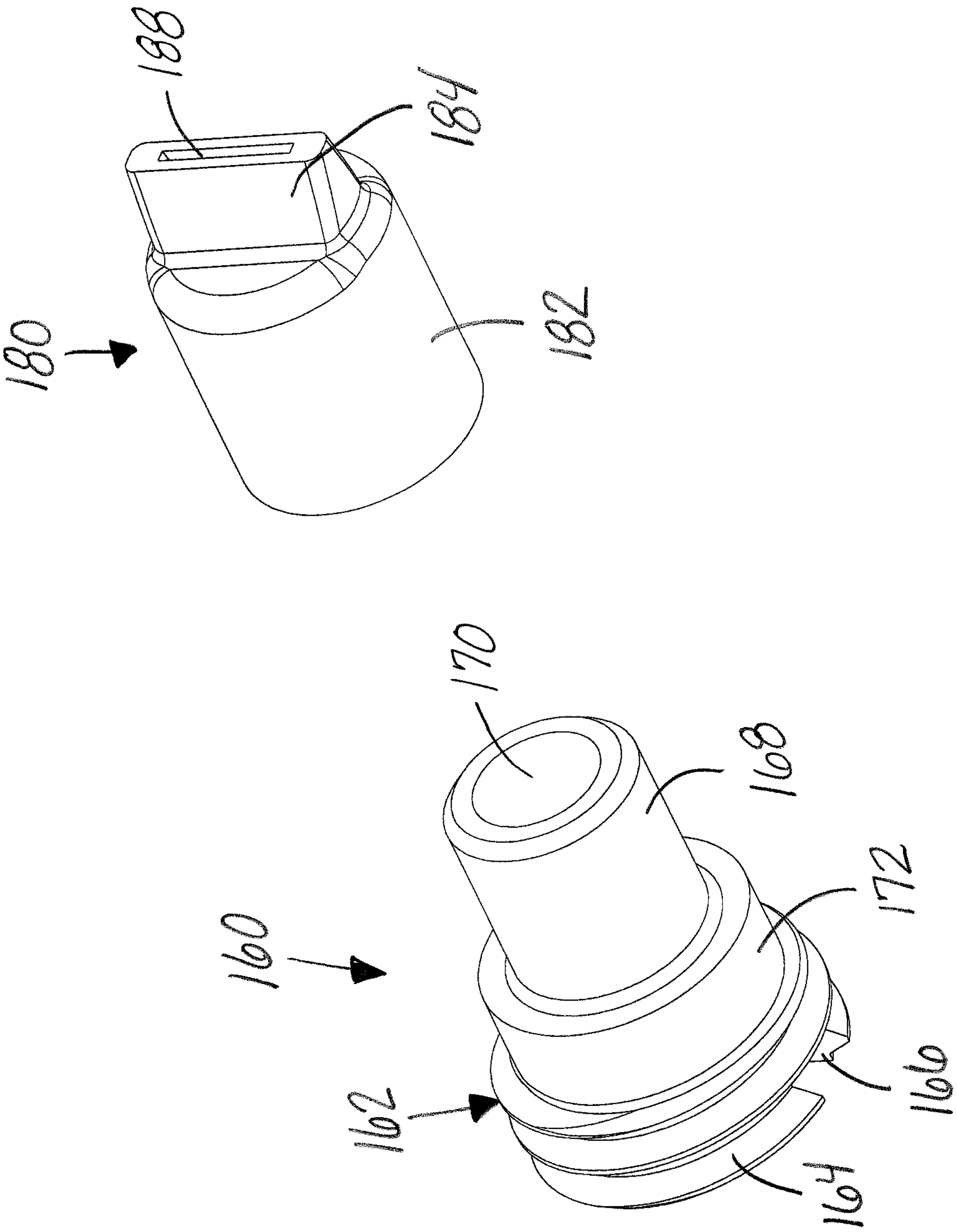
FIG. 17 is an exploded, second perspective view of the check valve system of FIG. 12, in accordance with an aspect of the present disclosure.
Figure 18:
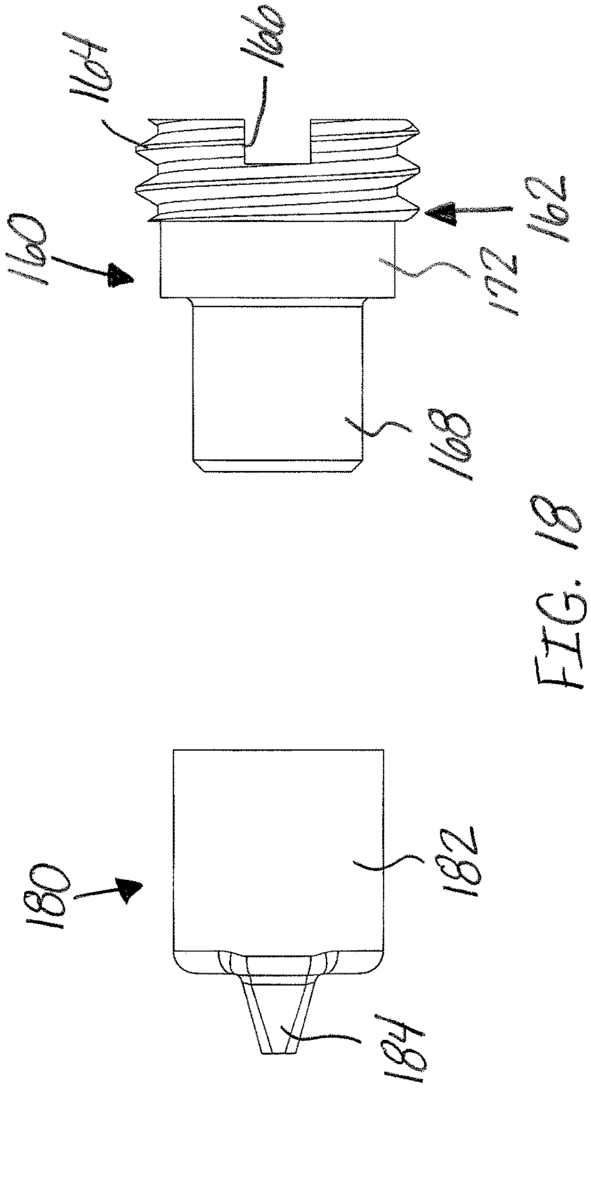
FIG. 18 is an exploded, side view of the check valve system of FIG. 12, in accordance with an aspect of the present disclosure.
Figure 19:
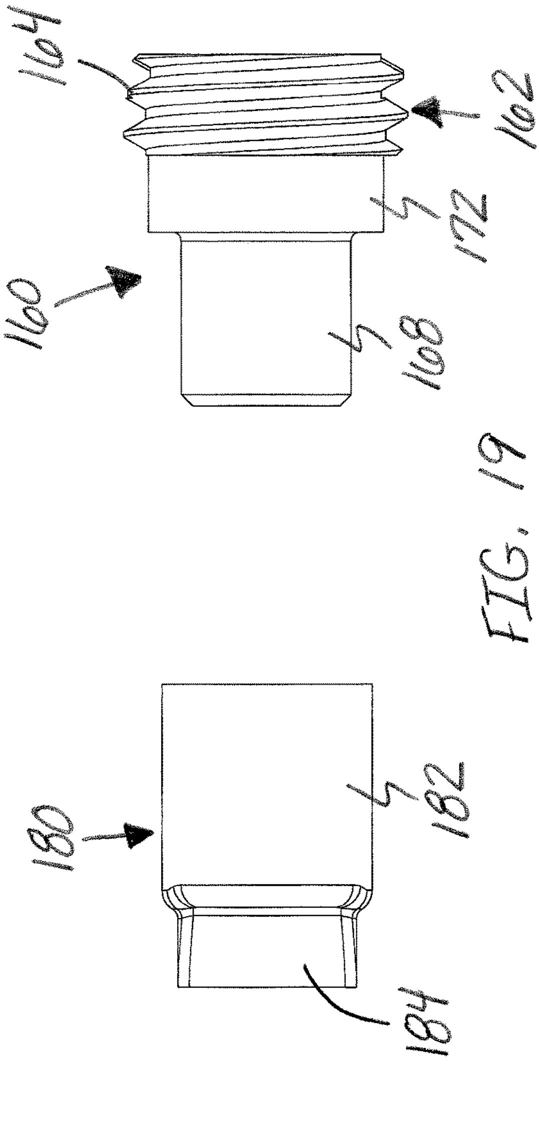
FIG. 19 is an exploded, top view of the check valve system of FIG. 12, in accordance with an aspect of the present disclosure.
Figure 20:
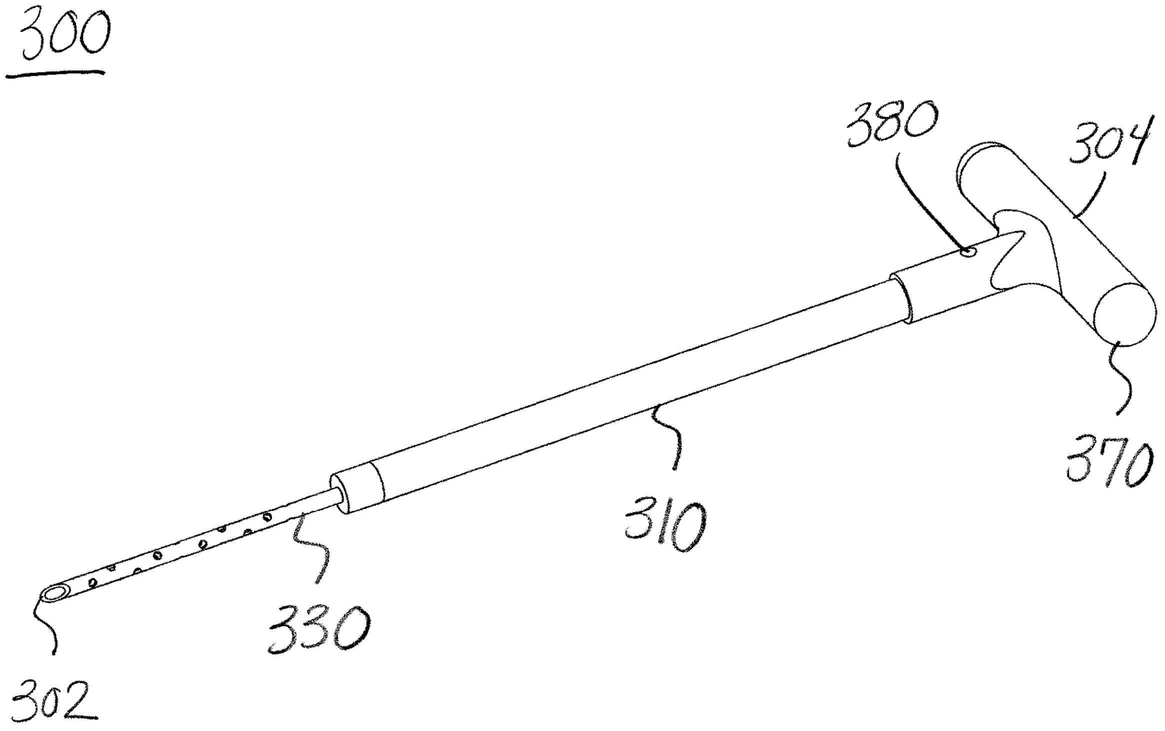
FIG. 20 is a first perspective view of another apparatus, in accordance with an aspect of the present disclosure.
Figure 21:
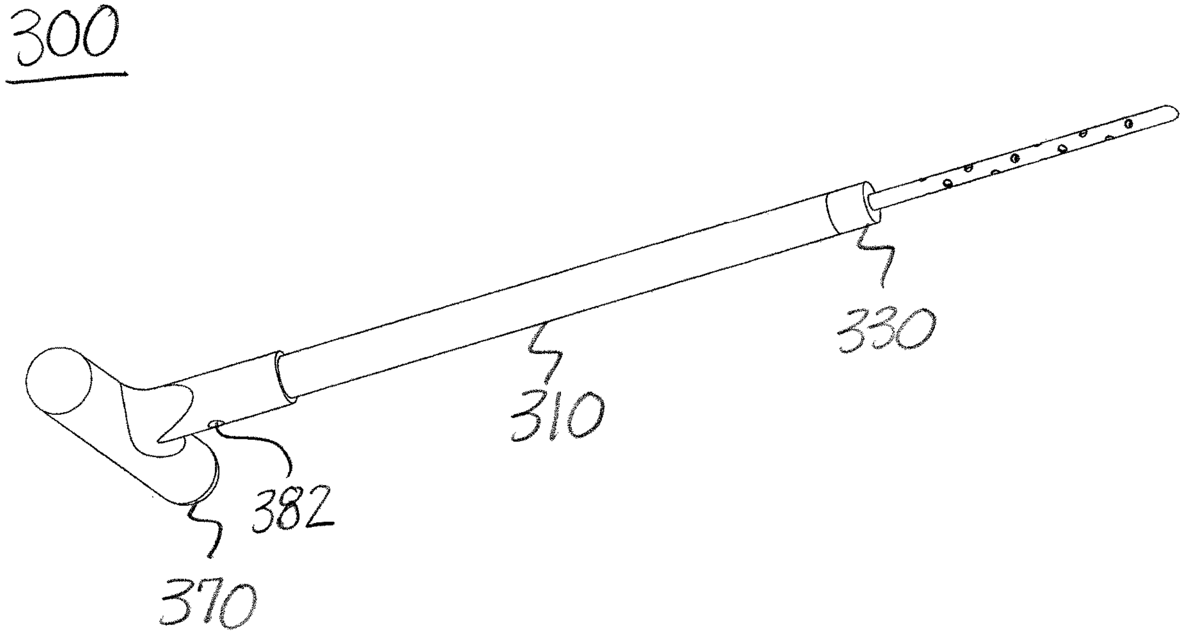
FIG. 21 is a second perspective view of the apparatus in accordance with an aspect of the present disclosure.
Figure 22:
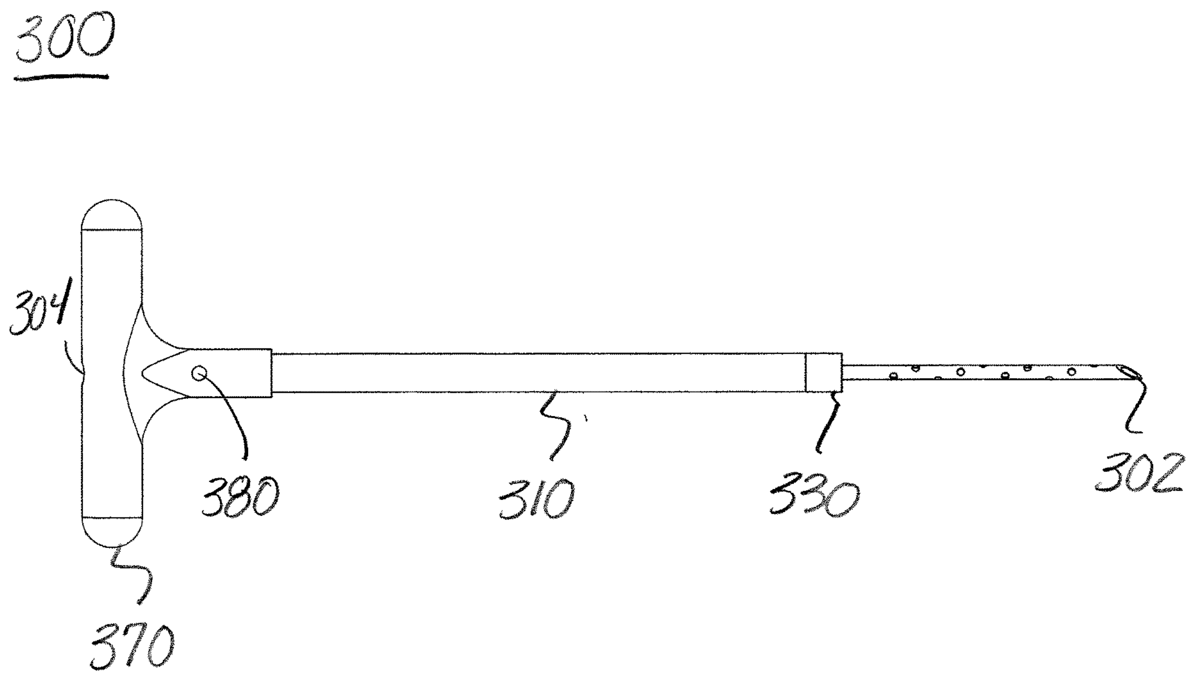
FIG. 22 is a top view of the apparatus in accordance with an aspect of the present disclosure.
Figure 23:
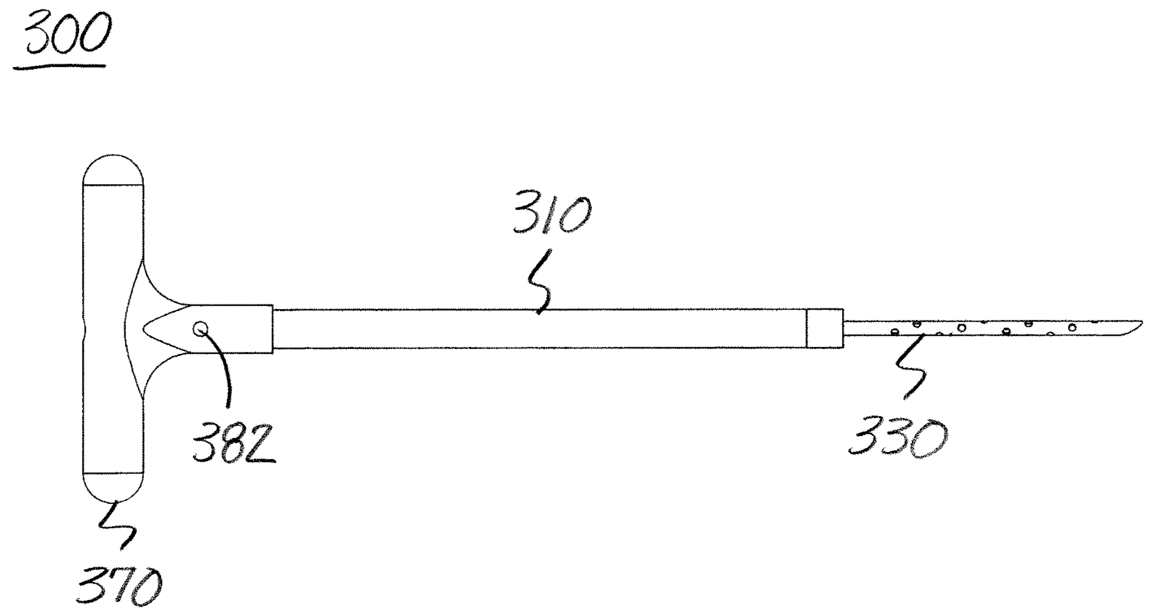
FIG. 23 is a bottom view of the apparatus in accordance with an aspect of the present disclosure.
Figure 24:
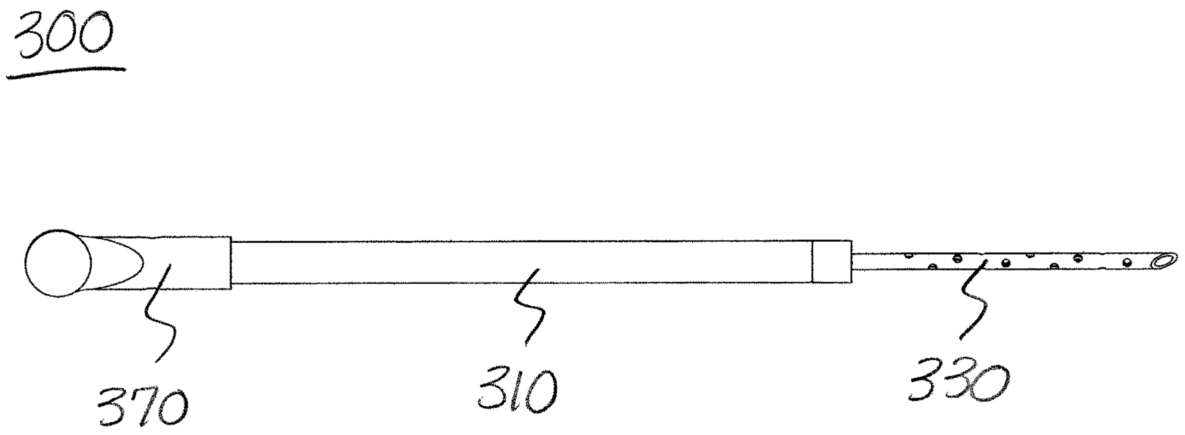
FIG. 24 is a first side view of the apparatus in accordance with an aspect of the present disclosure.
Figure 25:
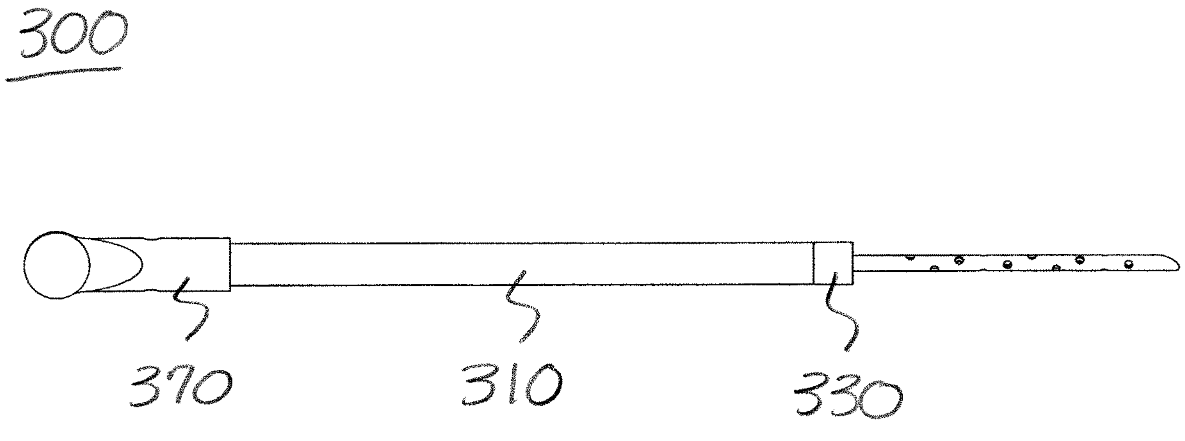
FIG. 25 is a second side view of the apparatus in accordance with an aspect of the present disclosure.
Figure 26:
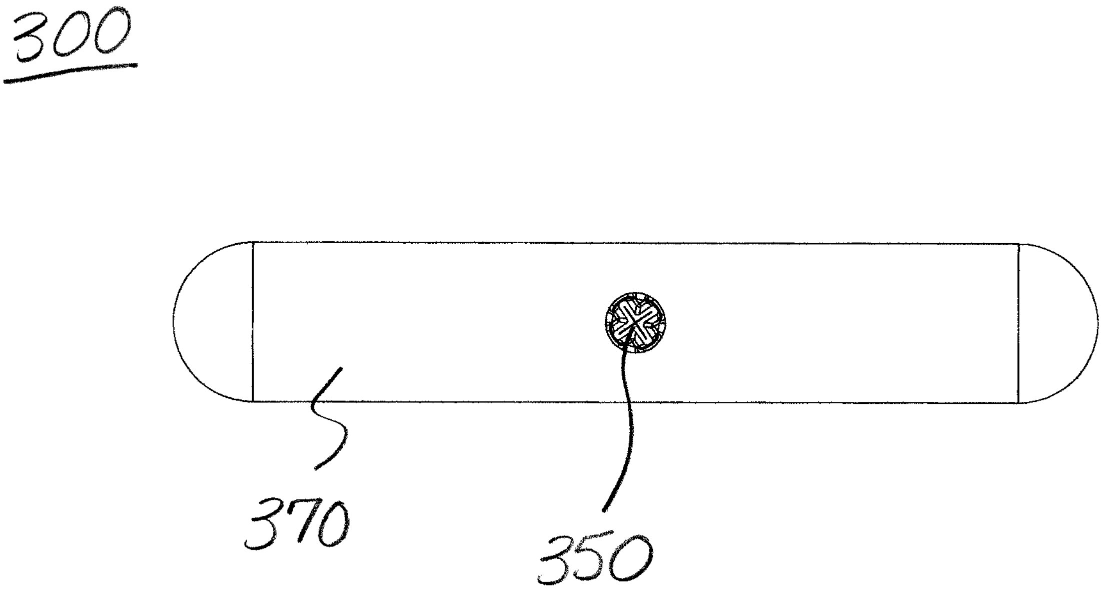
FIG. 26 is a first end view of the apparatus in accordance with an aspect of the present disclosure.
Figure 27:
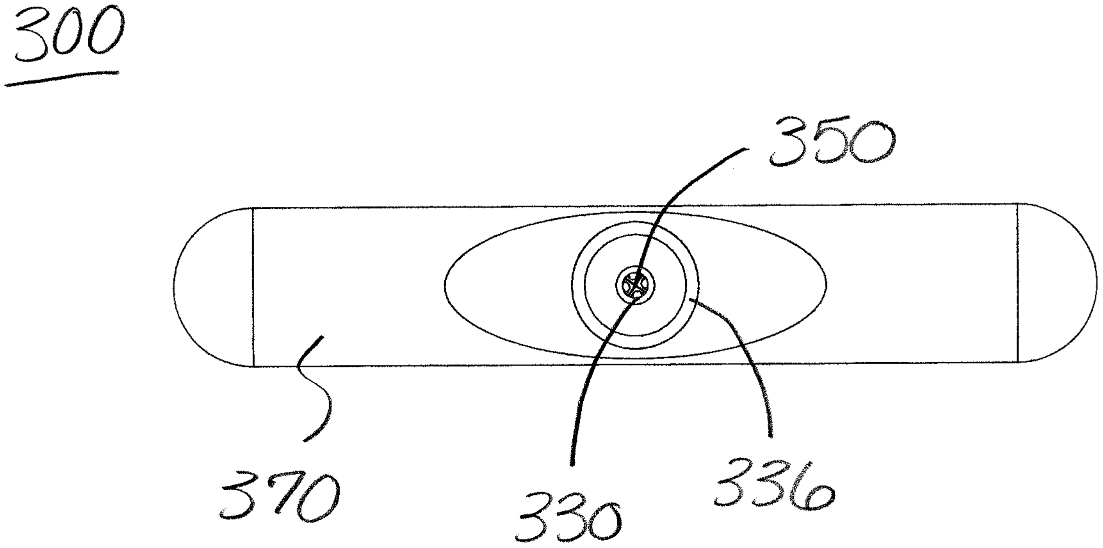
FIG. 27 is a second end view of the apparatus in accordance with an aspect of the present disclosure.
Figure 28:
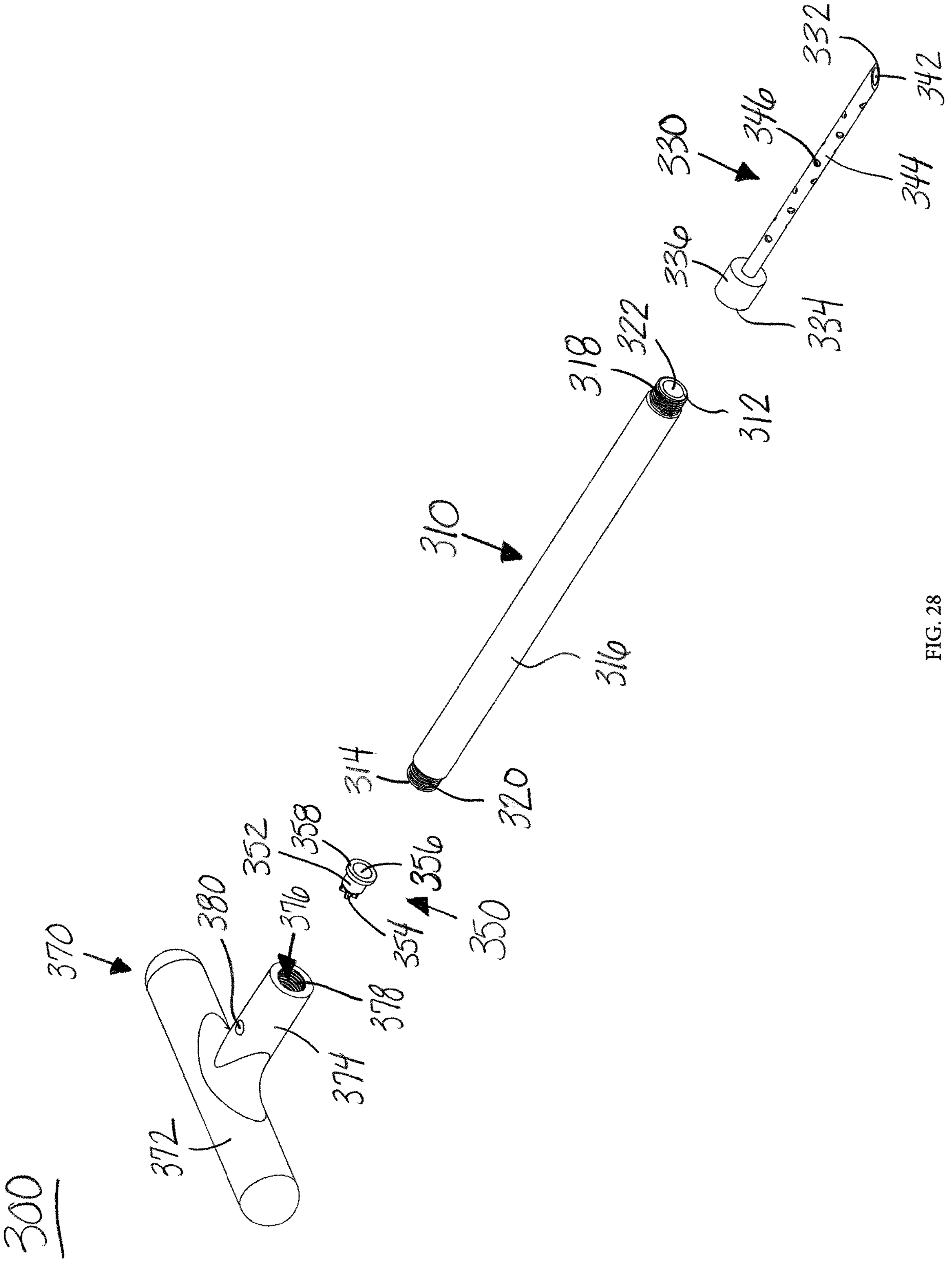
FIG. 28 is a first exploded, perspective view of the apparatus in accordance with an aspect of the present disclosure.
Figure 29:
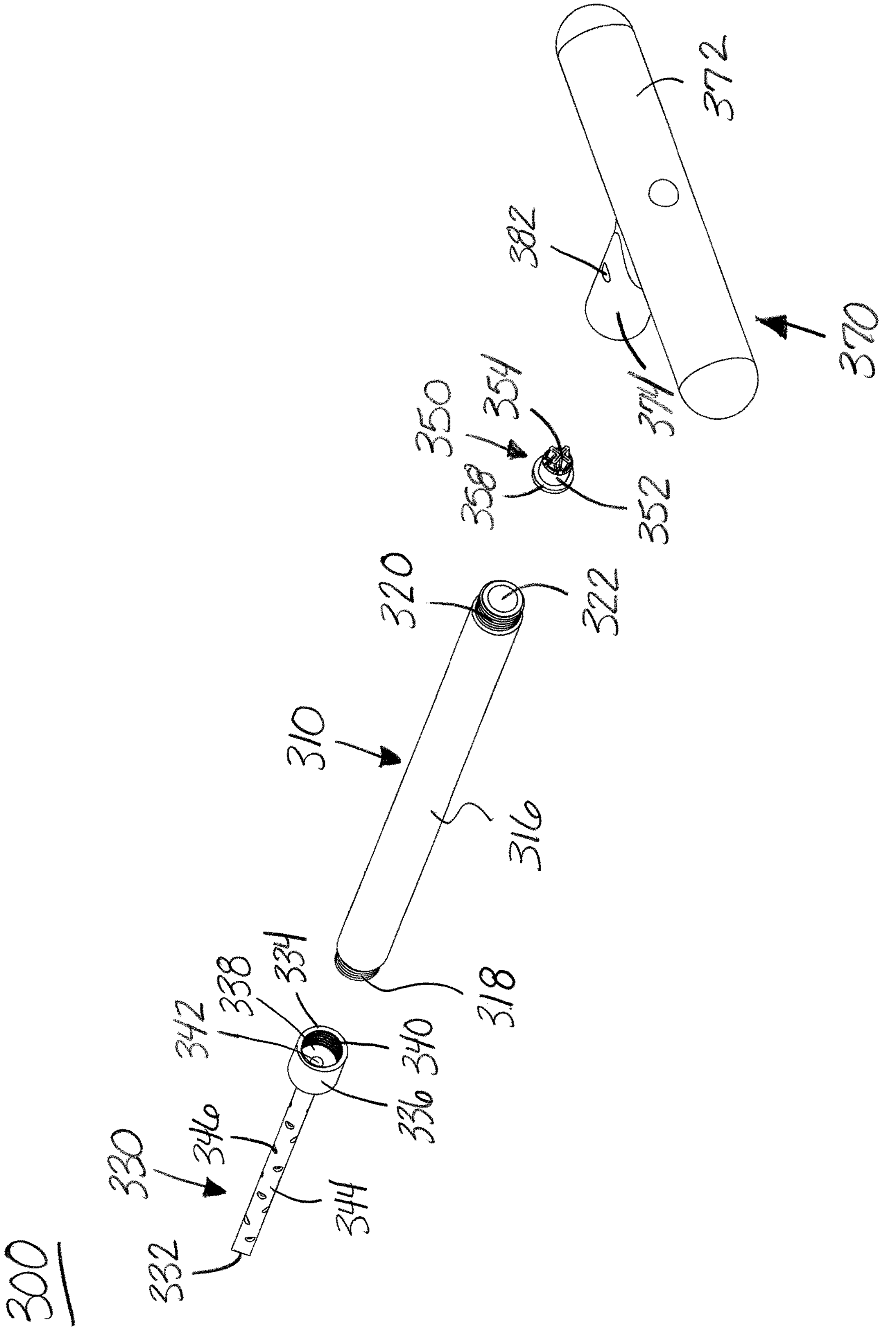
FIG. 29 is a second exploded, perspective view of the apparatus in accordance with an aspect of the present disclosure.
Figure 30:
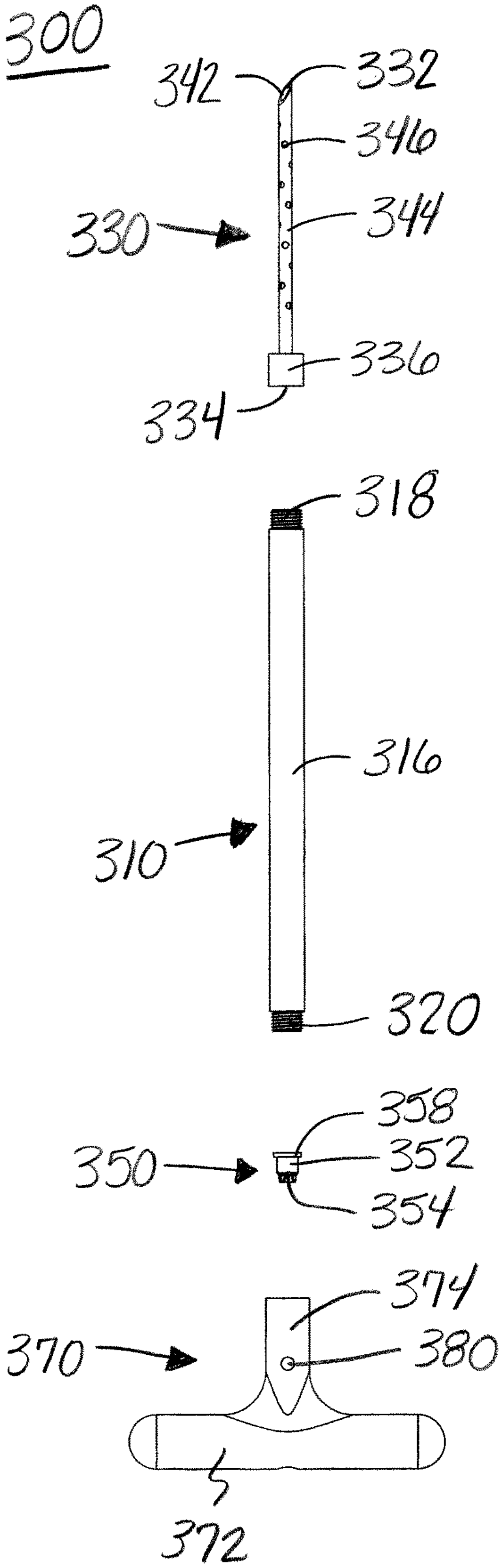
FIG. 30 is an exploded, top view of the apparatus in accordance with an aspect of the present disclosure.
Figure 31:
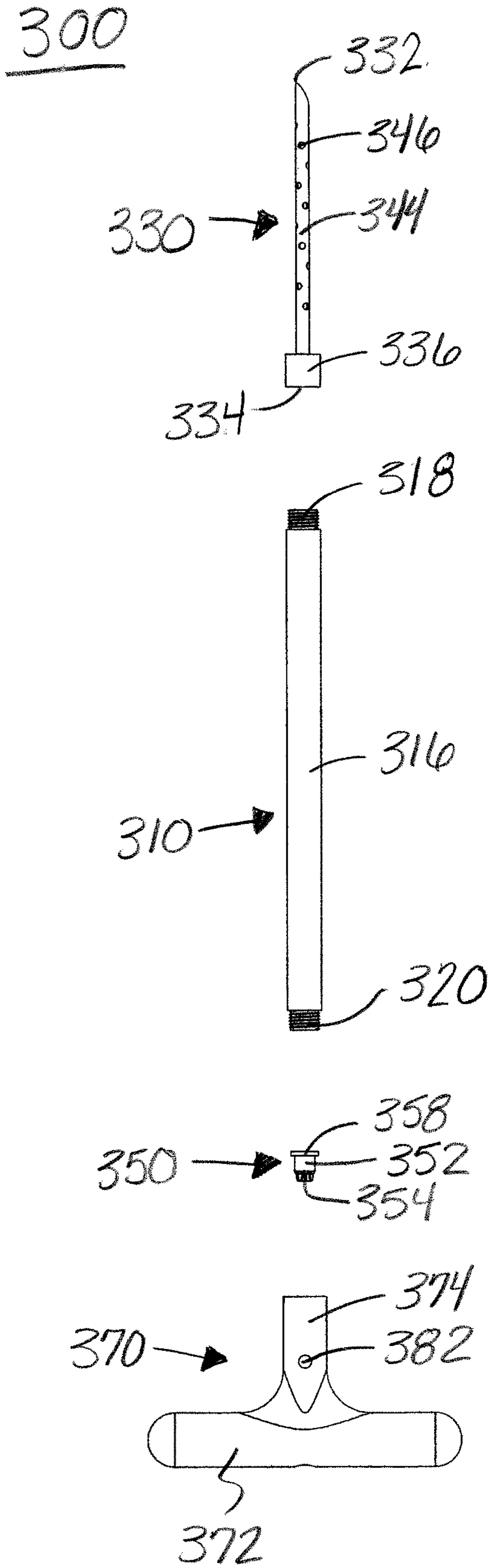
FIG. 31 is an exploded, bottom view of the apparatus in accordance with an aspect of the present disclosure.
Figure 32:
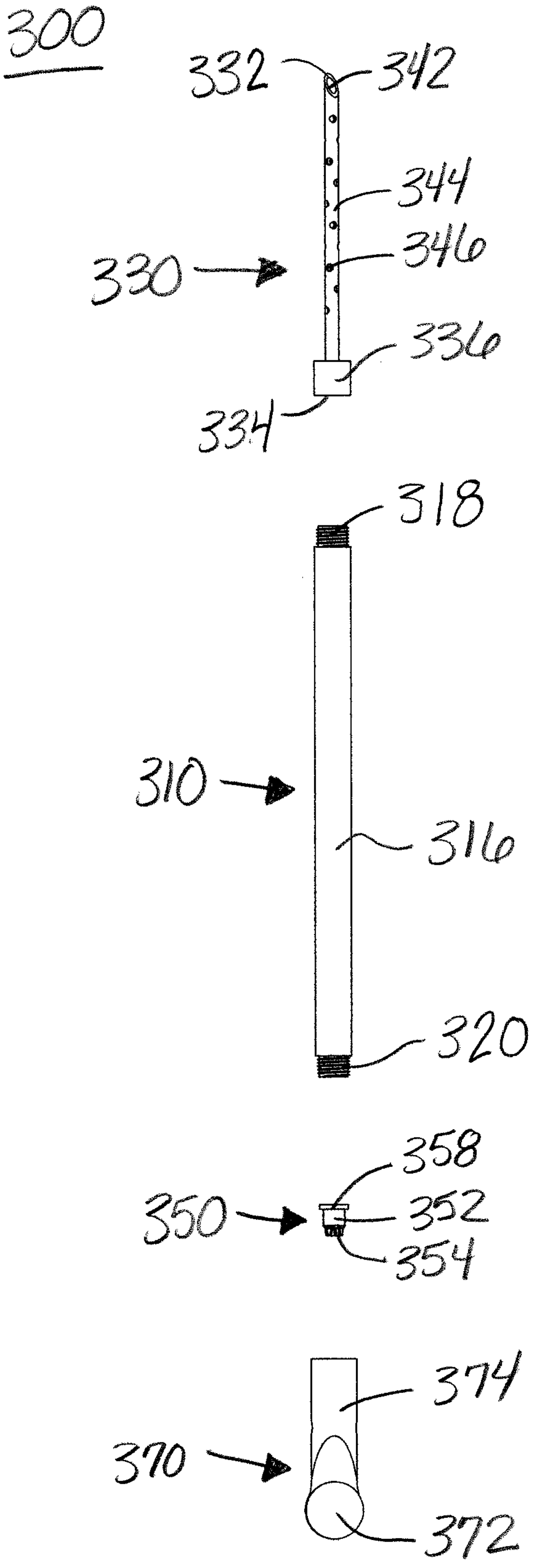
FIG. 32 is an exploded, first side view of the apparatus in accordance with an aspect of the present disclosure.
Figure 33:
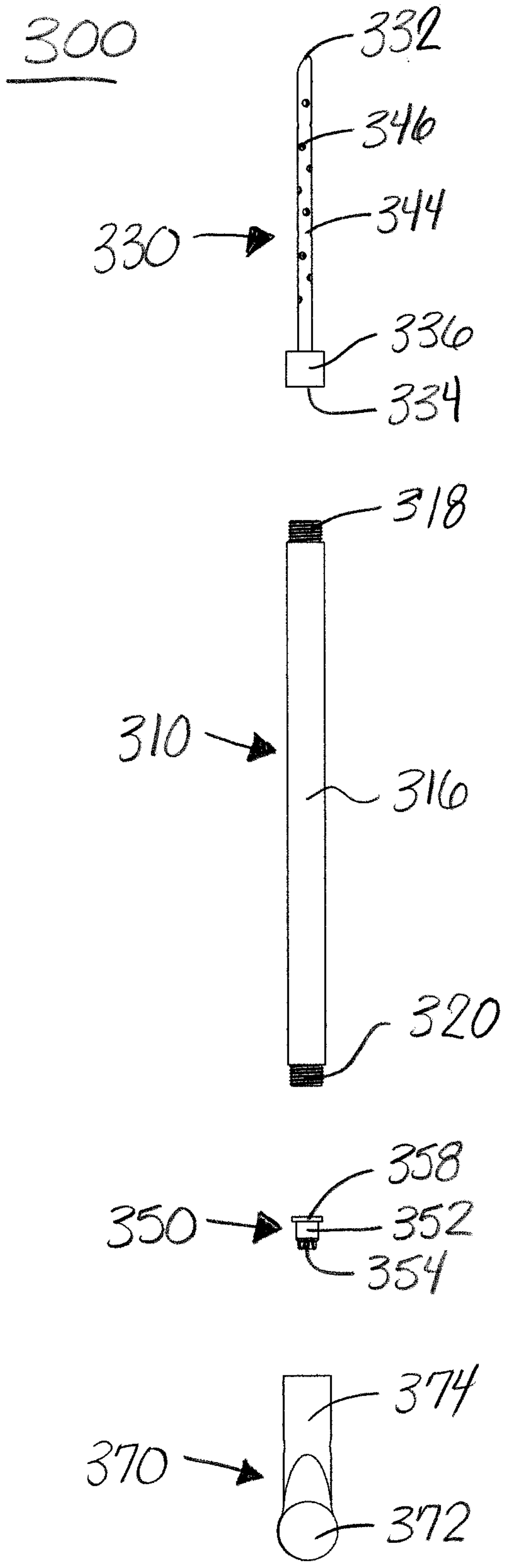
FIG. 33 is an exploded, second side view of the apparatus in accordance with an aspect of the present disclosure.
Figure 35:
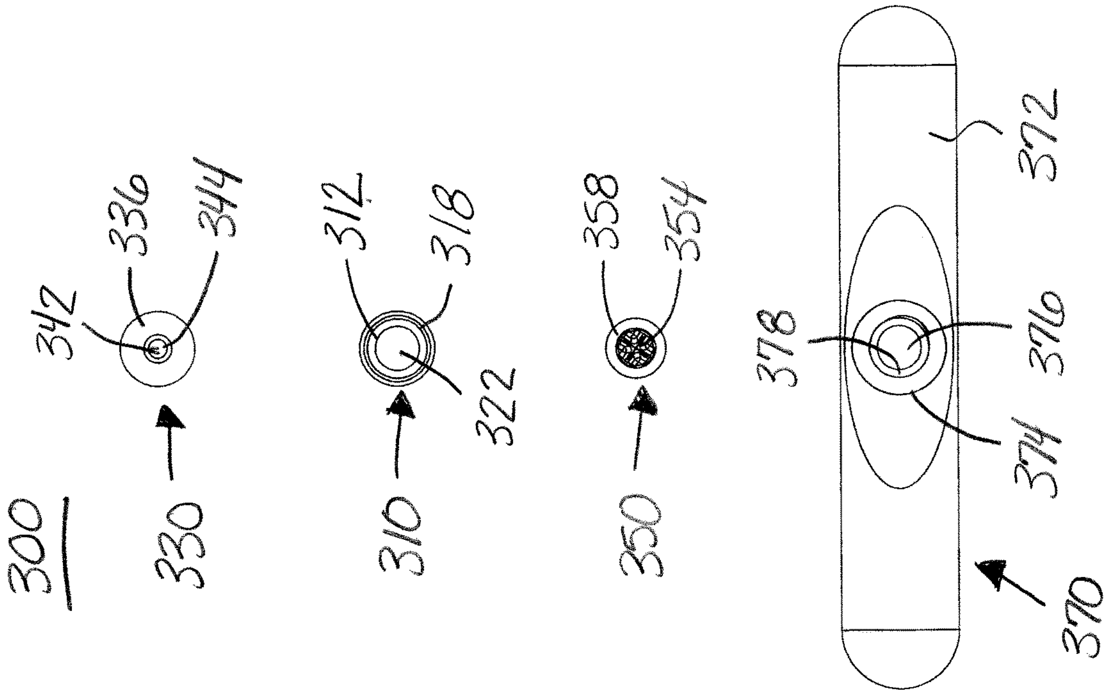
FIG. 35 is an exploded, second end view of the apparatus in accordance with an aspect of the present disclosure.
Figure 34:
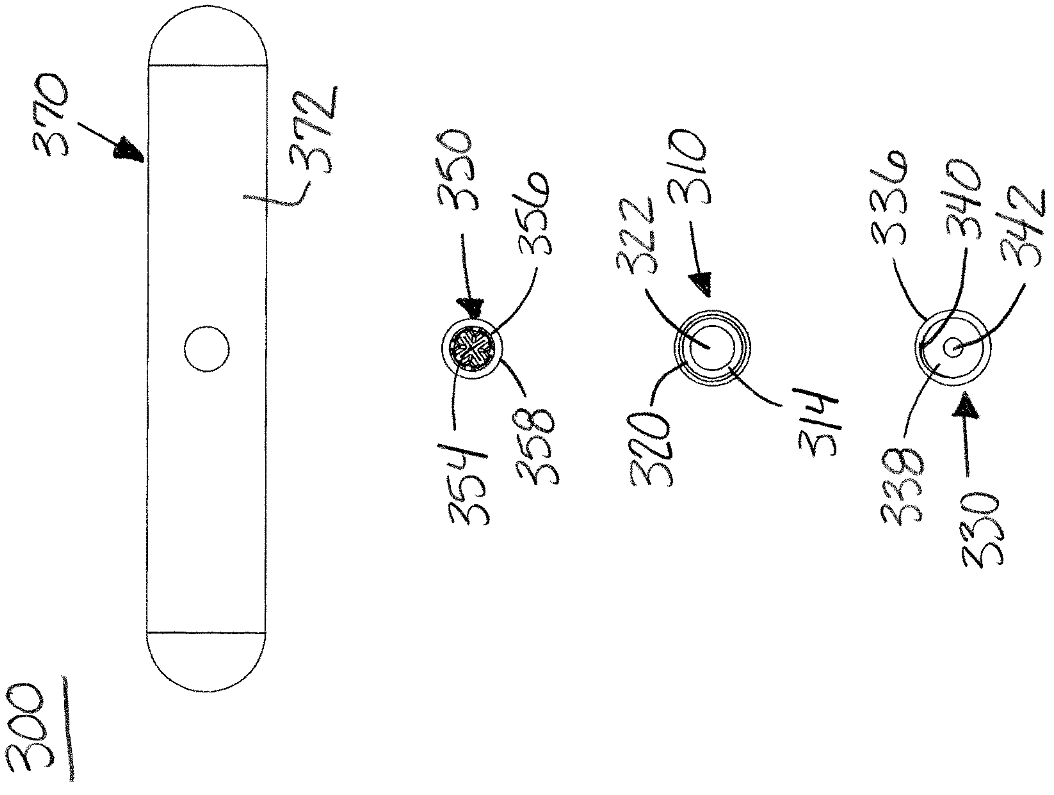
FIG. 34 is an exploded, first end view of the apparatus in accordance with an aspect of the present disclosure.

Generally stated, disclosed herein are apparatus, instruments, and systems for harvesting and/or collecting bone, tissue and fluids for bone graft harvesting, cancer biopsies, bone marrow aspirations, and the like. Further, methods for harvesting and/or collecting bone, tissue and fluids for bone graft harvesting, cancer biopsies, bone marrow aspirations are discussed.

In this detailed description and the following claims, the words proximal, distal, anterior or plantar, posterior or dorsal, medial, lateral, superior, and inferior are defined by their standard usage for indicating a particular part or portion of a bone, instrument, or apparatus according to the relative disposition of the natural bone or directional terms of reference. For example, "proximal" means the portion of an instrument nearest the torso, while "distal" indicates the portion of the instrument farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot, the term "dorsal" refers to the top of the foot and the term "plantar" refers to the bottom of the foot.

Referring to the drawings, wherein like reference numerals are used to indicate like or analogous components throughout the several views, and with particular reference to FIGS. 1-19, apparatus, instruments, systems, and methods of using the apparatus, instruments, and systems for harvesting and/or collecting bone, tissue, cells, and fluids for bone graft harvesting, cancer biopsies, bone marrow aspirations, and the like are shown.

Referring now to FIGS. 1-11, an apparatus, cutting apparatus, or instrument 100 is shown. The apparatus 100 includes a first end 102 and a second end 104. The apparatus 100 includes a cylinder 110, a cutting member 140, a securement member 160, a passive check valve 180, a shaft 190, and a distal cap or drive member 220. The cutting member 140 is coupled to a first end 112 of the cylinder 110. The shaft 190 is coupled to a second end 114 of the cylinder 110. The cutting member 140 may be permanently attached to the cylinder 110 on the first end 112 and the shaft 190 may be permanently attached to the cylinder 110 on a second end 114. Alternatively, the cutting member 140 and the shaft 190 may each be mechanically attached to the cylinder 110. Regardless of how the cutting member 140 and the shaft 190 are attached to the cylinder 110, they are connected in an airtight fashion. The distal cap 220 is removably coupled to the shaft 190. The securement member 160 and the valve 180 may be coupled together and received within the distal cap 220. The securement member 160 may be positioned adjacent to the cylinder 110.

With continued reference to FIGS. 1-11, the cylinder, collection chamber, or collection tube 110 including a first end 112 and a second end 114. The cylinder 110 may include a central housing 116 with a first attachment end 118 at the first end 112 and a second attachment end 124 at the second end 114. The attachment ends 118, 124 may have, for example, a diameter smaller than the diameter of the central housing 116. The cylinder 110 may also include a first recess 120 and a second recess 122 positioned opposite the first recess 120. The recesses 120, 122 may be positioned to overlap a portion of the central housing 116 and the first attachment end 118. The cylinder 110 may further include a third recess 126 and a fourth recess 128 positioned opposite the third recess 126. The recesses 126, 128 may be positioned to overlap a portion of the central housing 116 and the second attachment end 124. In an embodiment, the first and second recesses 120, 122 are positioned aligned with the third and fourth recesses 126, 128, respectively. The cylinder 110 may also include a through hole 130 extending through the cylinder 110 from a first end 112 to a second end 114. The through hole or hollow internal lumen 130 may be, for example, configured or sized and shaped to receive bone, bone graft and/or tissue.

The cylinder 110 may be, for example, clear or transparent to allow for visualization of the bone, tissue, and/or fluids being collected or harvested from a patient. The cylinder 110 may be, for example, a polycarbonate cylinder which may be round and/or clear. The cylinder 110 being clear or transparent permits visual assessment of collected material during bone, bone marrow, tissue, fat, and/or fluid harvesting from the body. The cylinder 110 may, for example, be entirely clear or transparent or, alternatively, have a portion along the length of the cylinder 110 which is clear or transparent.

The cutting member 140, as shown in FIGS. 1-11, may include a cutting end 142 and a coupling end 144. The coupling end 144 may include, for example, at least one protrusion 146, 148. The at least one protrusion may be, for example, two protrusion 146, 148 including a first protrusion 146 and a second protrusion 148. The first protrusion 146 may engage the first recess 120 and the second protrusion 148 may engage the second recess 122. The coupling end 144 may include a first opening 150 extending into the cutting member 140 from the coupling end 144. The cutting end 142 may also include a second opening 152 extending into the cutting member 140 from the cutting end 142. The second opening 152 may be, for example, at least one second opening 152. The cutting member 140 may also include a channel 154 extending through the cutting member 140 from the first opening 150 to the second opening 152. The cutting end 142 may also include a sharp edge extending along the second opening 152. The cutting member 140 may be, for example, a metal or stainless steel cutting tip. The cutting end 142 may be, for example, a continuous cutting blade running down from the tip down to a 180 degree bottom edge. In one embodiment, the cutting end 142 may have, for example, a helical shape extending distal to proximal to permit forward advancement without restriction. In another embodiment, the cutting end 142 may have, for example, at least one continual cutting blade along the entire distal tip opening to permit power-driven or manual cutting in either a clockwise or counter-clockwise directions, as well as a downward direction. The cutting end 142 may be, for example, two cutting blades angled relative to each other and meeting at or near the center of the cutting member 140. In yet other embodiments, the cutting end 142 may have, for example, a continuous cutting edge along the proximal edge continuing at an angle along a riser continuing uninterrupted to cutter blades at distal end forming one continuous cutting blade along the entire opening. The cutting member 140 may be, for example, permanently or removably attached to the collection tube 110.

It is also contemplated that the cutting member 140 of the instrument 100 may be replaced by a needle, hollow needle, Jam Shidi needles, and the like for performing cancer biopsies, bone marrow aspirations, and the like. These instruments may include needles at the first end as discussed in greater detail below.

Referring now to FIGS. 3-19, the securement member 160 and passive check valve 180 are shown. The securement member 160 may include a head 162 and a shaft 168 extending from the head 162. The head 162 may include threads or other fixation mechanisms 164 extending circumferentially around the first end of the head 162. The head 162 may also include an engagement channel 166 extending into the first end of the securement member 160. The engagement channel 166 extends across the diameter and through the center of the head 162. The securement member 160 may also include a through hole 170 extending through the securement member 160 from a first end to a second end. The securement member 160 may also include a protrusion 172 extending from the shaft 168 distal to the head 162. The head 162 of the securement member 160 may engage the second end 114 of the cylinder 110.

The passive check valve or valve 180 may include a body 182 and a valve member 184 extending from an end of the body 182. The body 182 includes a through hole 186 extending through the body from a first end to a second end. The valve 180 also includes a valve opening 188 extending into the valve member 184 and engaging the through hole 186 in the body 182. The through hole 186 is configured or sized and shaped to receive the shaft 168 of the securement member 160. When assembled, the first end of the valve 180 engages the protrusion 172. The coupled valve 180 and securement member 160 within the distal cap 220 is hermetically-sealed with the collection chamber 110 and cutting member 140. More specifically, a hermetically sealed system is created between the first end of the cutting member 140, the collection chamber 110, the shaft 190, and the distal cap 220 from the first end to the recessed channel 230 with the coupled valve 180 and securement member 160 contained within. The valve member 184 may be, for example, angled or tapered from the body 182 to the second end of the valve 180. The valve member 184 may be, for example, a valve that prevents backflow and allows for only one-way flow. The valve member 184 may be, for example, a duckbill valve, circular slit valve, umbrella style check valves either one-way or multi-directional manner for regulating airflow and minimizing or relieving vacuum pressure.

With continued reference to FIGS. 1-11, the shaft or step down shaft 190 is shown. The shaft 190 includes a first portion 192, a second portion 194, and a tapered portion 196 coupling and extending between the first portion 192 and the second portion 194. The diameter of the first portion 192 is smaller than the diameter of the second portion 194. The tapered portion 196 is angled or tapered between the first portion 192 and the second portion 194. The shaft 190 also includes a first opening 198 at the first end of the shaft 190 and extending into the first portion 192. The shaft 190 further includes a second opening 200 at the second end of the shaft 190 and extending into the second portion 194. The shaft 190 also includes a through hole 202 extending between the first opening 198 and the second opening 200. The second attachment end 124 of the cylinder 110 extends through the first opening 198 and into a portion of the through hole 202 within the first portion 192. The shaft 190 also includes a first protrusion 204 extending away from the first end of the first portion 192. In addition, the shaft 190 includes a second protrusion 206 extending away from the first end of the first portion 192 opposite the first protrusion 204. The protrusions 204, 206 are positioned to engage the recesses 126, 128 in the cylinder 110, respectively. The shaft 190 further includes a first coupling channel 208 and a second coupling channel 210 extending into the second end of the shaft 190. The first coupling channel 208 is positioned on a side of the shaft 190 opposite the second coupling channel 210. The channels 208, 210 may be, for example, a backward "L" shape.

The distal cap or drive member 220 is shown in FIGS. 1-11. The distal cap 220 includes a body 222 and a shaft 244 extending away from the body 222. The body 222 may include a first portion 224, a second portion 226, and a third portion 228. The first portion 224 is positioned at a first end of the body 222. The first portion 224 and the second portion 226 are separated by a recessed channel 230. The third portion 228 is positioned adjacent to the second portion 226. The body 222 also includes a first opening 232 and a second opening 234 extending into the third portion 228, as shown in FIGS. 4-7. The first opening 232 extends into the third portion 228 on a side opposite the second opening 234. The body 222 also includes a protrusion 236 extending away from the body 222 circumferentially. The protrusion 236 further includes a third opening 238 and a fourth opening 240 positioned opposite each other. The first opening 232 may be aligned with the third opening 238 and the second opening 234 may be aligned with the fourth opening 240. The openings 238, 240 may be, for example, open air vents to allow for the passage of air out of the instrument 100. The protrusion 236 may have a larger diameter than the diameter of each of the first portion 224, second portion 226, and third portion 228. The third portion 228 may also have a diameter larger than the diameter of the first portion 224 and the second portion 226. The body 222 may extend through the second opening 200 of the shaft 190 and the portions 224, 226, 228 of the drive member 220 received within a portion of the through hole 202. The body 222 also includes a cavity 242 extending into the first end of the drive member 220. The cavity 242 may receive the securement member 160 and the passive check valve 180. The cavity 242 may include threads to threadably engage the threads 164 of the securement member 160. The securement member 160 may alternatively be positioned within shaft 190 between the cylinder 110 and the drive member 220.

With continued reference to FIGS. 1-11, the shaft 244 extends away from a second end of the protrusion 236. The shaft 244 may also include an alignment portion 246 positioned near the second end of the shaft 244. The shaft 244 may have a diameter smaller than the diameters of the portions 224, 226, 228 and protrusions 236. The drive member 220 may also include a first coupling member 250 and a second coupling member 252. The first coupling member 250 may be received within the first opening 232 and the second coupling member 252 may be received within the second opening 234. The coupling members 250, 252 may be received within the coupling channels 208, 210 of the shaft 190 to removably secure the drive member 220 to the shaft 190. The drive member 220 may further include an O-ring 254. The O-ring 254 may be received within the recessed channel 230 of the drive member 220. In an embodiment, the O-ring 254 seals the airflow between the first end of the drive member 220 and the second end shaft coupler 190 which is permanently affixed and sealed to the collection tube 110. Although the O-ring 254 is shown being attached to the drive member 220, it is also contemplated that the O-ring 254 may be coupled to another component, such as, the interior of the shaft coupler 190. The collection tube 110 may also be hermetically-sealed to the shaft coupler 190.

A surgical method for harvesting bone graft material using the instrument 100 may include coupling the instrument 100 to a rotation tool. The method also includes selecting a bone for harvesting the bone graft material and preparing the selected bone. The surgical procedure may be performed on a living patient or a cadaver. The instrument 100 may be positioned at the selected bone and then the rotation tool or driver may be activated to transmit torque from the tool to the collection chamber 110 and the cutting member 140. As the driver is activated bone graft material is cut and moved into the collection chamber 110. During insertion of the cutting member 140 into the bone, air flows up, through the second end 104 of the instrument 100, and exits the drive member 220 through the openings 238, 240. The tool may apply uni-directional or multi-directional cutting and grinding of the bone from the harvest site. Rotational and downward forces are applied to the instrument 100 to cut and collect bone into the interior collection chamber 110 for use in orthopedic, podiatry, neurosurgical, and oncology biopsy procedures. Once the bone is drilled, the instrument 100 may be removed from the patient. As the instrument 100 is removed a vacuum phenomena can be experienced by the collection chamber 110. During proximal removal of the instrument 100, the passive check valve 180 of the instrument 100 passively closes off air flow in the opposite direction creating and maintaining an equal pressure at the proximal end of the collection chamber 110 to that of the pressure within the harvest site to prevent the vacuum phenomena from pulling the bone graft material out of the collection chamber 110 during removal of the instrument 100 from the patient. Thus, the collection of bone graft material can be maximized with each pass of the instrument 100 by minimizing bone graft loss due to vacuum forces through the distal cutting tip during removal from the harvest site. By minimizing the number of passes needed to obtain the desired amount of bone graft, tissue, or cells, the amount of tissue loss and/or damage, bleeding, bone stresses, pain, and surgical time may be decreased.

Referring now to FIGS. 20-38, another instrument 300 is shown. The instrument 300 includes a collection chamber 310, a needle portion 330, a passive check valve 350, and a handle 370. The instrument 300 includes a first end 302 and a second end 304. The needle portion 330 is positioned at the first end 302 of the instrument 300 and the handle 370 is positioned at the second end 304 of the instrument 300. The collection chamber 310 couples to the needle portion 330 on one end and the handle 370 is coupled to the collection chamber 310 on the other end. As shown, the valve 350 is positioned between the collection chamber 310 and the handle 370. However, it is also contemplated that the valve 350 may be positioned between the collection chamber 310 and the needle portion 350.

With continued reference to FIGS. 20-35, the collection chamber 310 includes a first end 312 and a second end 314. The collection chamber 310 includes a central housing 316 extending between the first end 312 and the second end 314. The collection chamber 310 also includes a first attachment end 318 at the first end 312 and a second attachment end 320 at the second end 314. The attachment ends 318, 320 may be, for example, threaded or include an alternative attachment mechanism as known by one of skill in the art. In addition, the collection chamber 310 has a through hole 322 extending through the chamber 310 from the first end 312 to the second end 314.

Figure 36:
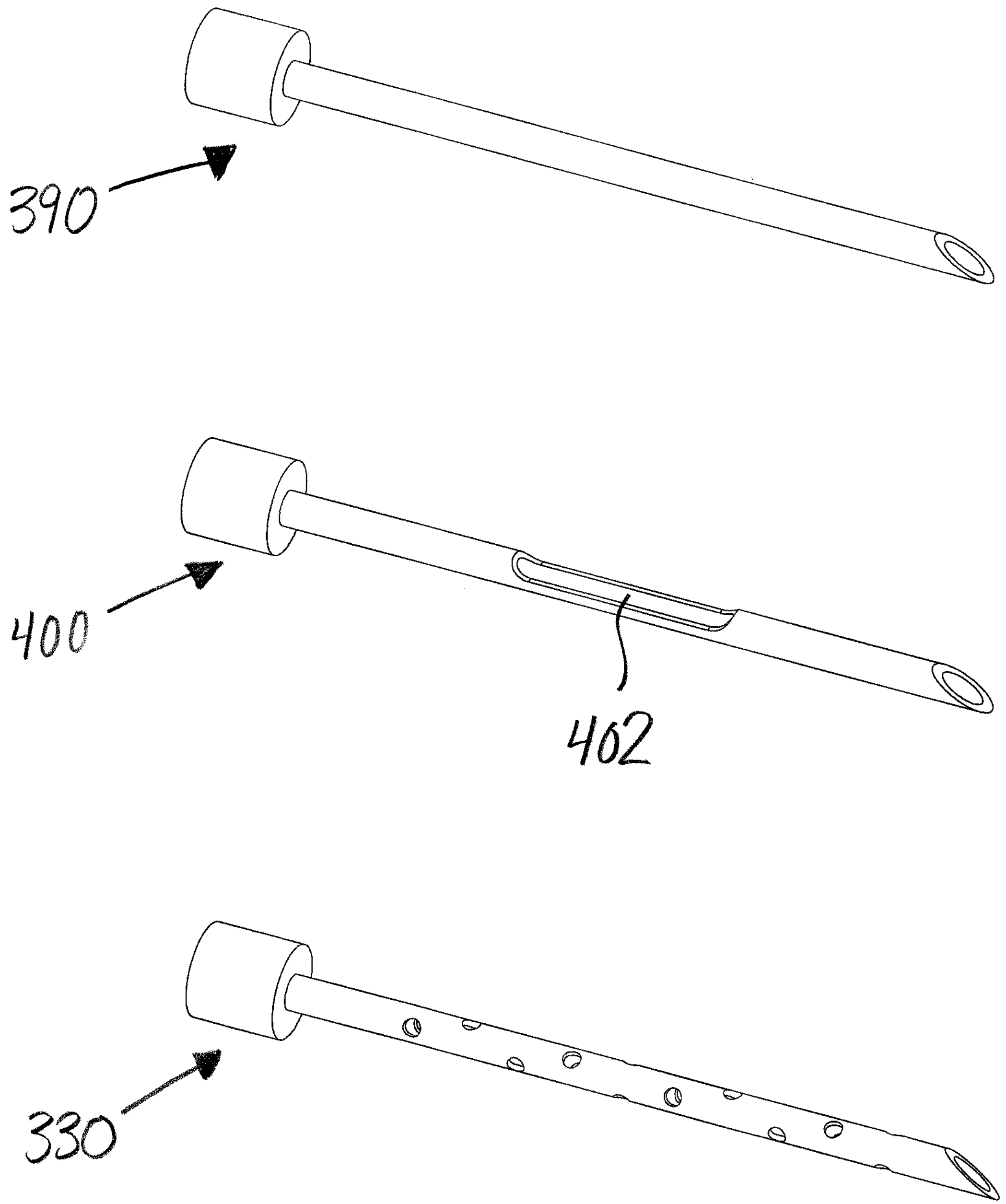
FIG. 36 are perspective views of needle portions of the apparatus in accordance with an aspect of the present disclosure.
Figure 37:
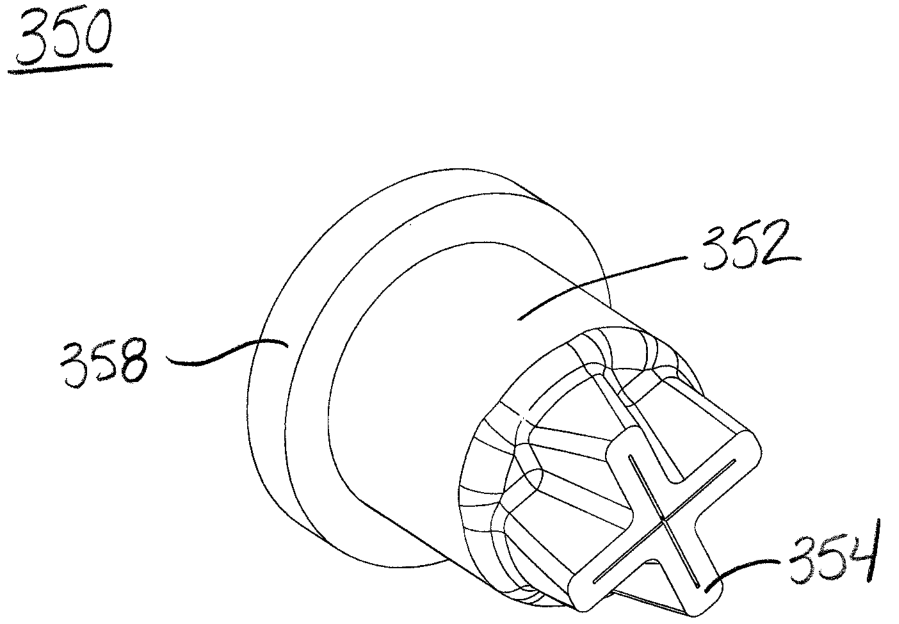
FIG. 37 is a first perspective view of the check valve system of FIG. 20, in accordance with an aspect of the present disclosure.
Figure 38:
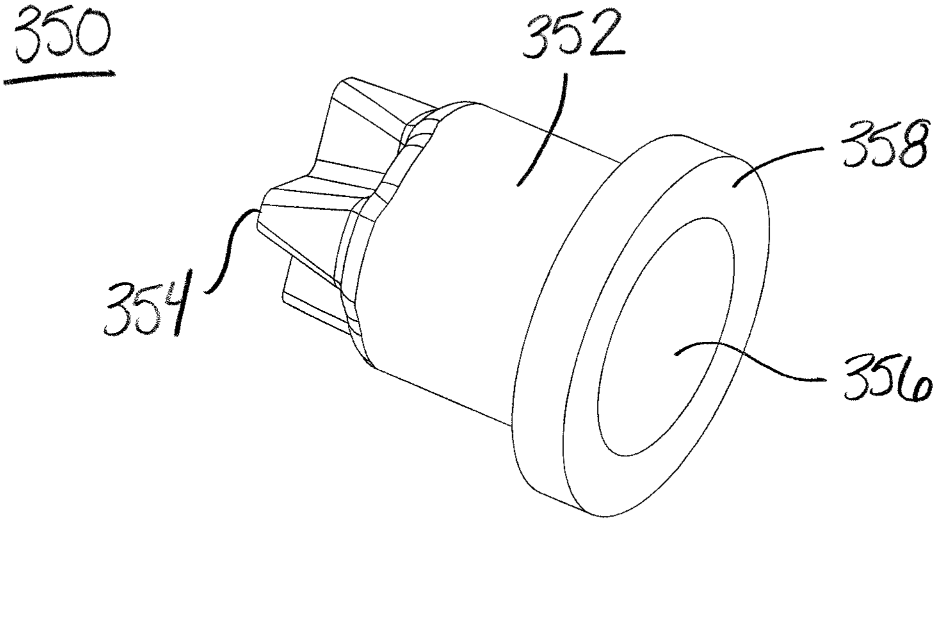
FIG. 38 is a second perspective view of the check valve system of FIG. 20, in accordance with an aspect of the present disclosure.

In addition, as shown in FIGS. 20-35, the needle portion 330 includes a first end 332 and a second end 334. The needle portion 330 includes a head 336 at the second end 334 and a shaft 344 extending from the head 336 to the first end 332. The head 336 may include an opening 338 extending into the head 336 from the second end 334. The opening 338 may also include threads 340 on the interior surface of the opening 338. The threads 340 may be, for example, configured or sized and shaped to engage the threads of the first attachment end 318. The needle portion 330 may also include a through hole 342 extending from the opening 338 to the first end 332 through the shaft 344. The shaft 344 may include, for example, a plurality of holes 346 extending from the exterior of the shaft 344 to the through hole 342. In alternative embodiments, as shown in FIG. 36, a needle portion 390, similar to the needle portion 330, the shaft 344 may be, for example, solid or without any holes 346. In yet other embodiments, a needle portion 400, similar to the needle portion 330, however, the shaft 344 includes, for example, an elongated opening 402 inset into a portion of the shaft 344. The elongated opening 402 may be positioned near, for example, a midpoint of the shaft 344. The elongated opening 403 may have, for example, an oval or rectangular shape. The first end 332 of the shaft 344 may be, for example, angled, tapered, or in other embodiments that are closed. The through hole 342 of the needle portion 330 may extend into the through hole 322 of the collection chamber 310.

As shown in FIGS. 28-35 and 37-38, the passive check valve 350 is shown. The valve 350 includes a body 352 with a valve member 354 at a one end. The valve 350 also includes a through hole 356 extending through the body 352 and the valve member 354. The valve member 354 may be, for example, a duckbill valve, umbrella valve, dome valve, cross-slit valve, mini valve balls, x-fragm dispensing valve, and/or combination umbrella and duckbill valve. The valve 350 may also include a protrusion 358 extending circumferentially away from another end of the body 352. The protrusion 358 may surround the through hole 356. As shown, the valve 350 may be positioned, for example, within the handle 370. The protrusion 358 may be positioned to sit directly on the second end 314 of the collection chamber 310 and within the handle 370 when the handle 370 is attached to the collection chamber 310. Although not shown, the valve 350 may alternatively be positioned, for example, within the head 336 of the needle portion 330 and the through hole 322 of the collection chamber 310. In this embodiment, the protrusion 358 of the valve 350 may be inserted into the opening 338 of the needle portion 330 and at least a portion of the body 352 and valve member 354 are positioned within the through hole 322 of the collection chamber 310.

The handle 370, as shown in FIGS. 20-35, may include a first portion 372 and the second portion 374 extending away from a midpoint of the first portion 372. The first portion 372 may be, for example, positioned perpendicular to the second portion 374. The second portion 374 may include an opening 376 extending into the second portion 374 from a first end. The opening 376 may include threads 378 along at least a portion of the opening 376. The threads 378 may be, for example, configured or sized and shaped to engage or correspond to the threads of the second attachment end 320 of the cylinder 310. The second portion 374 may also include a first hole 380 extending from an exterior surface of the second portion 374 into the opening 376. The second portion 374 may also include a second hole 382 extending from the exterior surface of the second portion 374 into the opening 376. The first hole 380 may be positioned opposite the second hole 382. The holes 380, 382 allow for air to be released from the interior of the instrument 300 during insertion and/or removal of the instrument 300 from a patient. Although two holes 380, 382 are shown, it is also contemplated that any number of holes 380, 382 may be positioned in the second portion 374 to allow for release of air from the instrument 300 during use. The first portion 372 may also include a through hole extending through the first end of the handle 370 into the opening 376. The through hole may be, for example, configured or sized and shaped to attach a syringe and/or vacuum to the instrument 300. Although not shown, it is also contemplated that the instrument 300 may also include a securement member 160 for coupling to the check valve 350. In this alternative embodiment, the opening 376 may include a double thread (not shown) with a first portion coupling to the threads 164 of the securement member 160 and the second portion coupling to the threads of the second end 320 of the cylinder 310.

Another surgical method for performing a needle biopsy with an instrument 300 including a biopsy needle is shown in FIGS. 20-36. The method also includes preparing the biopsy site and positioning the biopsy needle at the biopsy site. Then, the needle may be inserted into the biopsy site and the tissues, cells and/or bone marrow collected by distally directional forces or application of dissection instrumentation extracting the tissues, cells and/or bone marrow from the patient into the collection chamber 310. During insertion of the needle 330, 390, 400 into the biopsy site, air flows up, through the instrument 300, and exits the handle 370 through the holes 380, 382. Once the tissues, cells or bone marrow are collected in the collection chamber 310, the instrument 300 may be removed from the patient. As the instrument 300 is removed a vacuum phenomena is experienced by the collection chamber 310. During proximal removal of the instrument 300, the passive check valve 350 of the instrument 300 passively closes off air flow in the opposite direction creating and maintaining an equal pressure at the proximal end of the collection chamber 310 to that of the pressure within the harvest site to prevent the vacuum phenomena from pulling the cells, tissues, or bone marrow out of the collection chamber 310 during removal of the instrument 300 from the patient. Thus, the collection of cells, tissues, or bone marrow for a biopsy or bone marrow aspiration can be maximized with each sample removal with the instrument 300 by minimizing tissues, cells or bone marrow loss through the distal needle tip during removal from the harvest site. By minimizing the number of biopsy samples needed to obtain the desired amount of cells, tissue, or bone marrow, the amount of tissue loss, damage, bleeding, bone stresses, and surgical time may be decreased.

Given the illustrated examples above, the present disclosure provides in one aspect an apparatus 100, 300, comprising: a cylinder 110, 310 with a first end 112, 312 and a second end 114, 314; a passive check valve 180, 350 with a first end and a second end, wherein the passive check valve 180, 350 is positioned at at least one of the first end and the second end of the cylinder 110, 310; and a harvesting member 140, 330, 390, 400 coupled to the first end 112, 312 of the cylinder 110, 310.

Some embodiments of the apparatus 100, 300 further comprise: a securement member 160 with a first end and a second end.

In some embodiments of the apparatus 100, 300 of the first end of the securement member 160 engages the second end of the cylinder 110.

In some embodiments of the apparatus 100, 300 of the second end of the securement member 160 couples to the first end of the passive check valve 180.

In some embodiments of the apparatus 100, 300 of the harvesting member 140 comprises: a cutting tip 142 coupled to the first end 112 of the cylinder 110.

In some embodiments of the apparatus 100, 300 further comprise: a shaft 190 coupled to the second end 114 of the cylinder 110.

In some embodiments of the apparatus 100, 300 further comprise: a drive member 220 removably coupled to the second end of the shaft 190.

In some embodiments of the apparatus 100, 300 of the passive check valve 180, 350 comprises: a body 182, 352; and a valve member 184, 354 coupled to and extending from the body 182, 352.

In some embodiments of the apparatus 100, 300 of the cylinder 110, 310 is transparent.

In some embodiments of the apparatus 100, 300 of the harvesting member 330, 390, 400 comprises: a biopsy needle 330, 390, 400 coupled to the first end 312 of the cylinder 310.

In some embodiments of the apparatus 300 of the biopsy needle 330, 390, 400 comprises: a through hole 342 extending from a first end 332 to a second end 334 of the biopsy needle 330, 390, 400; and at least one hole 346 extending through the biopsy needle 330, 390, 400 from an exterior surface to the through hole 342.

In some embodiments of the apparatus 300 of the at least one hole 346 comprises a plurality of holes 346.

In a further aspect of the illustrated examples above, the present disclosure provides a harvesting system, comprising: an apparatus 100, 300, wherein the apparatus 100, 300 comprises: a cylinder 110, 310 with a first end 112, 312 and a second end 114, 314; a passive check valve 180, 350 with a first end and a second end, wherein the passive check valve 180, 350 is positioned at at least one of the first end 112, 312 and the second end 114, 314 of the cylinder 110, 310; and a harvesting member 140, 330, 390, 400 coupled to the first end 112, 312 of the cylinder 110, 310; and a removal attachment coupled to the apparatus 100, 300.

In some embodiments of the harvesting system of the removal attachment is a driver tool coupled to the apparatus 100, 300.

In some embodiments of the harvesting system of the driver tool is selected from a drill or electric screwdriver.

In some embodiments of the harvesting system of the harvesting member 140 comprises: a cutting tip 142 coupled to the first end 112 of the cylinder 110.

In some embodiments of the harvesting system of the harvesting member comprises: a biopsy needle 330, 390, 400 coupled to the first end 312 of the cylinder 310.

In some embodiments of the harvesting system of any one of the cylinder 110, 310 is transparent.

As may be recognized by those of ordinary skill in the art based on the teachings herein, numerous changes and modifications may be made to the above-described and other embodiments of the present disclosure without departing from the scope of the disclosure. The components of the instruments as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the instruments may include more or fewer components or features than the embodiments as described and illustrated herein. Accordingly, this detailed description of the currently-preferred embodiments is to be taken in an illustrative, as opposed to limiting of the disclosure.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The disclosure has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the disclosure be construed as including all such modifications and alterations.

What is claimed is:

1. A surgical method for harvesting bone graft material, comprising:

obtaining a harvesting system including a drive member and a transparent cylinder with a first end and a second end, a cutting member located at the first end of the cylinder, a shaft coupled to the second end of the cylinder, the drive member removably coupled to the shaft, and a one-way valve positioned at the first end of the cylinder so as to permit flow in one direction but prevent flow in a reverse direction;

positioning a cutting member at a bone of a patient selected for harvesting;

activating a rotation tool coupled to the drive member so as to transmit torque to the cylinder and the cutting member;

cutting bone graft material from the bone and receiving the bone graft material into the cylinder during rotation of the cutting member;

flowing air up, through a second end of the apparatus, and exiting the drive member through at least one opening in the drive member during distal movement of the cutting member into the bone; and removing the apparatus from the patient while the one-way valve passively closes off air flow in the opposite direction to maintain equal pressure in the cylinder and the harvest site to prevent the bone graft material from being pulled out of the cylinder during removal.

2. The surgical method of claim 1, wherein the one-way valve comprises a body and a valve member coupled to and extending from the body, the valve member including at least one of a duckbill valve, a circular slit valve, and an umbrella style check valve.

3. The surgical method of claim 1, further including coupling a securement member between the second end of the cylinder and a first end of the one-way valve, the securement member engaging the cylinder and the one-way valve to secure the one-way valve at the end of the cylinder.

4. The surgical method of claim 1, wherein the cutting member comprises a cutting end having a helical shape extending from a distal end to a proximal end of the cutting member.

5. The surgical method of claim 1, wherein the cutting member comprises a cutting end having at least one continual cutting blade along an entire distal tip opening to permit power-driven cutting in at least one of a clockwise or counter-clockwise direction.

6. The surgical method of claim 1, wherein activating the rotation tool applies at least one of uni-directional or multi-directional cutting and grinding of a bone from the harvest site.

7. The surgical method of claim 1, wherein the drive member includes a protrusion extending circumferentially from the drive member, the protrusion comprising at least two openings positioned opposite each other through which air exits during distal movement of the cutting member.

8. The surgical method of claim 1, wherein the cylinder comprises a polycarbonate material that permits visual assessment of collected bone graft material during harvesting.

* * * * *